(12) United States Patent
Zambach et al.

(10) Patent No.: US 8,722,578 B2
(45) Date of Patent: *May 13, 2014

(54) SPIROHETEROCYCLIC PYRROLIDINEDIONE HERBICIDAL COMPOSITIONS

(75) Inventors: Werner Zambach, Stein (CH); Ottmar Franz Hueter, Stein (CH); Jean Wenger, Wallbach (CH); Marcela Goeghova, Bratislava (SK); Thomas Pitterna, Stein (CH); Peter Maienfisch, Stein (CH); Stephane André Marie Jeanmart, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 125 days.

This patent is subject to a terminal disclaimer.

(21) Appl. No.: 13/128,133

(22) PCT Filed: Oct. 28, 2009

(86) PCT No.: PCT/EP2009/064214
§ 371 (c)(1),
(2), (4) Date: Sep. 21, 2011

(87) PCT Pub. No.: WO2010/052161
PCT Pub. Date: May 14, 2010

(65) Prior Publication Data
US 2012/0004105 A1 Jan. 5, 2012

(30) Foreign Application Priority Data
Nov. 6, 2008 (GB) .................................. 0820344.0

(51) Int. Cl.
*A01N 43/36* (2006.01)
*A01N 43/40* (2006.01)
*A01N 43/90* (2006.01)
*C07C 35/31* (2006.01)
*C07C 39/14* (2006.01)
*C07D 209/54* (2006.01)
*C07D 221/20* (2006.01)
*C07D 401/02* (2006.01)
*C07D 471/10* (2006.01)

(52) U.S. Cl.
USPC ........... 504/129; 504/130; 504/138; 504/189; 504/244; 504/246; 504/248; 504/254; 504/283; 504/284; 514/183; 514/184; 514/278; 514/315; 514/320; 514/409; 514/421; 546/16; 548/400; 548/410; 560/8; 560/19; 560/45; 560/51

(58) Field of Classification Search
USPC ......... 504/129, 130, 138, 189, 244, 246, 248, 504/254, 283, 284; 514/183, 184, 278, 315, 514/320, 409, 421; 546/16; 548/400, 410; 560/8, 19, 45, 51
See application file for complete search history.

(56) References Cited

U.S. PATENT DOCUMENTS

| | | | |
|---|---|---|---|
| 5,981,567 A * | 11/1999 | Fischer et al. | 514/409 |
| 8,415,369 B2 * | 4/2013 | Zambach et al. | 514/278 |
| 2004/0009999 A1 * | 1/2004 | Fischer et al. | 514/278 |
| 2007/0298968 A1 * | 12/2007 | Bretschneider et al. | 504/221 |

FOREIGN PATENT DOCUMENTS

| | | |
|---|---|---|
| WO | 9501358 | 1/1995 |
| WO | 2009049851 | 4/2009 |

* cited by examiner

*Primary Examiner* — Jane C Oswecki
(74) *Attorney, Agent, or Firm* — R. Kody Jones

(57) ABSTRACT

Herbicidal compositions containing as active ingredients spiroheterocyclic pyrrolidine dione compounds.

6 Claims, No Drawings

SPIROHETEROCYCLIC PYRROLIDINEDIONE HERBICIDAL COMPOSITIONS

This application is a 371 of International Application No. PCT/EP2009/064214 filed Oct. 28, 2009, which claims priority to GB 0820344.0 filed Nov. 6, 2008, the contents of which are incorporated herein by reference.

The present invention relates to novel herbicidal compositions containing as active ingredient spiroheterocyclic pyrrolidine diones or derivatives thereof and to the use of these compounds in controlling grasses and weeds, especially in crops of useful plants, or in inhibiting undesired plant growth.

Spiroheterocyclic pyrrolidine dione compounds having herbicidal action are described, for example, in WO9501358.

It has now been found that further alkoxy substituted spiroheterocyclic pyrrolidine diones or derivatives thereof can be used in herbicidal and growth-inhibiting compositions.

The present invention accordingly relates to novel herbicidal compositions containg in addition to comprising formulation adjuvants, a herbicidally effective amount of a compound of formula I

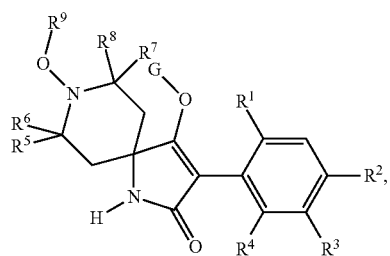

(I)

wherein
G is hydrogen or an agriculturally acceptable metal, sulfonium, ammonium or latentiating group,
$R^1$ is hydrogen, methyl, ethyl, n-propyl, iso-propyl, halomethyl, haloethyl, halogen, vinyl, ethynyl, methoxy, ethoxy, halomethoxy or haloethoxy, cyclopropyl or halogenocyclopropyl,
$R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl,
$R^4$ is hydrogen, methyl, ethyl, n-propyl, iso-propyl, halomethyl, haloethyl, halogen, vinyl, propenyl, ethynyl, propynyl, methoxy, ethoxy, halomethoxy or haloethoxy,
$R^5$, $R^6$, $R^7$ and $R^8$, independently of each other, are hydrogen or methyl,
$R^9$ is hydrogen, $C_1$-$C_6$alkyl, $C_1$-$C_6$haloalkyl, $C_1$-$C_6$cyanoalkyl, benzyl, $C_1$-$C_4$alkoxy($C_1$-$C_4$)alkyl, $C_1$-$C_4$alkoxy($C_1$-$C_4$)alkoxy($C_1$-$C_4$)alkyl or a group selected from G, or an agrochemically acceptable salt or N-oxide thereof.

In the substituent definitions of the inventively used compounds of the formula I, each alkyl moiety either alone or as part of a larger group (such as alkoxy, alkylthio) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

Cycloalkyl includes preferably cyclopropyl, cyclobutyl, cyclopentyl and cyclohexyl.

The term "heteroaryl" preferably refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Another group of preferred heteroaryls comprises furyl, thienyl, pyrazolyl, 1,2,3-triazolyl, 1,2,4-triazolyl, pyridyl, pyrimidinyl, pyridazinyl, pyrazinyl, quinolinyl, isoquinolinyl, cinnolinyl, quinazolinyl or quinoxalinyl.

The invention relates also to herbicidal compositions containing the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_a R_b R_c R_d)]OH$, wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_e R_f R_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O=C=C=O unit.

The inventively used compounds of formula I also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^1$— $R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

The inventively used compounds of formula I may exist in different geometric or optical isomers or different tautomeric forms. One or more centres of chirality may be present, in which case compounds of the formula I may be present as pure enantiomers, mixtures of enantiomers, pure diastereomers or mixtures of diastereomers. Centres of tautomerisation may be present. This invention covers the herbicidal use of all such isomers and tautomers and mixtures thereof in all proportions as well as isotopic forms such as deuterated compounds.

Preferred herbicidal compositions according to the invention are those wherein in the compounds of formula I $R^1$ methyl, ethyl, n-propyl, vinyl, ethynyl, halogen, methoxy, ethoxy, halomethoxy, haloethoxy, $R^2$ is methyl, halogen, methoxy, ethoxy, halomethoxy, haloethoxy, phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^3$ is hydrogen, $R^4$ is methyl ethyl, n-propyl, vinyl or ethynyl, $R^5$, $R^6$, $R^7$ and $R^8$ are hydrogen, and $R^9$ is hydrogen, $C_1$-$C_6$alkyl, $C_1$-$C_4$alkoxy ($C_1$-$C_4$)alkyl, $C_1$-$C_4$alkoxy($C_1$-$C_4$)alkoxy($C_1$-$C_4$)alkyl or a group selected from G, where those herbicidal compositions are particularly preferred wherein in the compound of the formula I $R^1$ is methyl and $R^2$ is methyl.

The inventively used compounds may be made by a variety of methods. For example, the compounds of formula I, wherein the substituents have the meanings assigned to them above, can be prepared by means of processes known per se, e.g. by treating compounds of formula (A) with an alkylating, acylating, phosphorylating or sulfonylating agent G-Q in the presence of at least one equivalent of a base, where G is the alkyl, acyl, phosphoryl or sulfonyl group to be incorporated and Q is a nucleofuge:

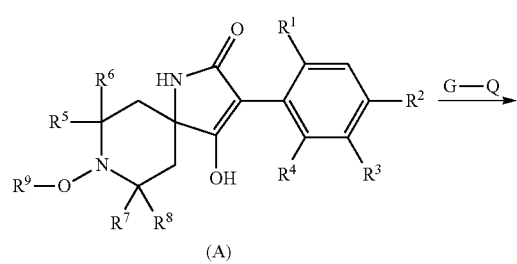

(A)

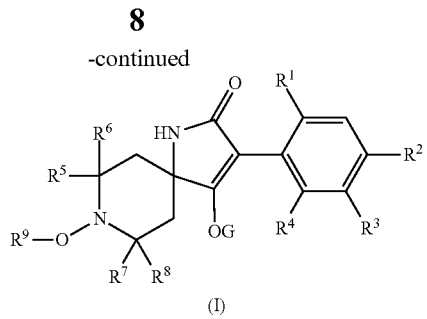

(I)

Compounds of formula I, wherein G is a latentiating group of the formula CM-$R^a$, C($X^b$)—$X^c$—$R^b$, C($X^d$)—N($R^c$)—$R^d$ may be prepared by known procedures as described, for example, in U.S. Pat. No. 6,774,133, U.S. Pat. No. 6,555,567 and U.S. Pat. No. 6,479,489. Typically, compounds of formula (A) are treated with an acylating agent such as an acid halide (especially acid chloride), acid anhydride, haloformate (especially chloroformate), halothioformate (especially chlorothioformate), isocyanate, isothiocycanate, carbamoyl halide (especially carbamoyl chloride) or thiocarbamoyl chloride (especially thiocarbamoyl chloride) in the presence of at least one equivalent of a suitable base, optionally in the presence of a suitable solvent. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases, where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane and acetonitrile. Suitable procedures are described, for example, in U.S. Pat. No. 6,774,133, U.S. Pat. No. 6,555,567 and U.S. Pat. No. 6,479,489.

Compounds of formula I, wherein G is a latentiating group of the formula C($X^b$)—$X^c$—$R^b$, C($X^d$)—N($R^c$)—$R^d$, may be also be prepared by treating compounds of formula II with phosgene or a phosgene equivalent, optionally in the presence of a solvent such as toluene or ethyl acetate, and a base and reacting the resultant chloroformate, or equivalent, with an alcohol, thiol or amine under known conditions, as described, for example, in U.S. Pat. No. 6,774,133, U.S. Pat. No. 6,555,567 and U.S. Pat. No. 6,479,489.

Compounds of formula I, wherein G is a latentiating group of the formula —$SO_2$—$R^e$, may be prepared by reaction of compounds of formula II with an alkyl or aryl sulfonyl halide, preferably in the presence of at least one equivalent of base.

Compounds of formula I, wherein G is a latentiating group of the formula —P($X^e$)($R^f$)—$R^g$ may be prepared from compounds of formula II using procedures described, for example, in U.S. Pat. No. 6,774,133, U.S. Pat. No. 6,555,567 and U.S. Pat. No. 6,479,489.

Compounds of formula I, wherein G is $C_1$-$C_6$alkyl, $C_2$-$C_6$alkenyl, $C_3$-$C_6$alkynyl or a latentiating group of the formula $CH_2$—$X^f$—$R^b$, may be prepared by treatment of a compound of formula II with a compound of formula G-Y wherein Y is a halogen (especially bromine or iodine), sulfonate (especially mesylate or tosylate) or a sulfate preferably in the presence of a base, under known conditions.

Compounds of formula (B)

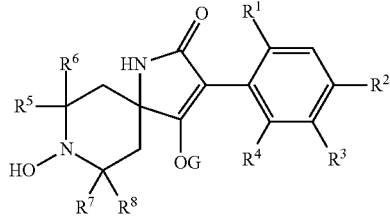

(B)

can be obtained by catalytic hydrogenation of compounds of formula I, in which R is represented by a benzyl group.

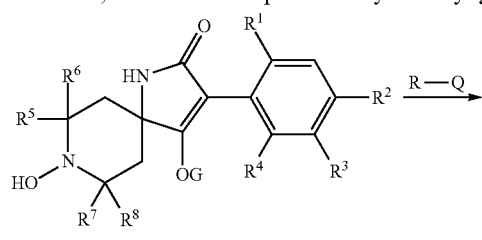

(B)

(I)

Compounds of formula I, in which R represents $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$, can be obtained by treating compounds of formula (B) with an alkylating, acylating, phosphorylating or sulfonylating agent R-Q, wherein Q represents a nucleofuge, in the presence of at least one equivalent of a base.

Suitable conditions are the same as described above for the conversion of compounds of formula (A) to compounds of formula I.

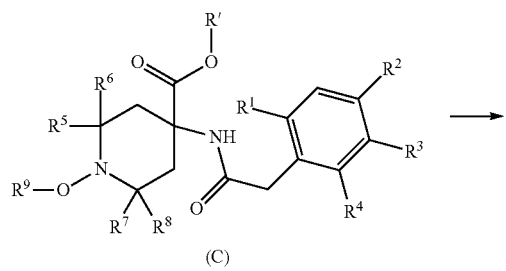

(C)

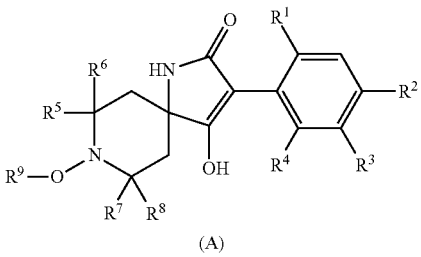

(A)

Compounds of formula (A) may be prepared via the cyclisation of compounds of Formula (C), preferably in the presence of base, and optionally in the presence of a suitable solvent, by methods described, for example, in U.S. Pat. No. 6,774,133, U.S. Pat. No. 6,555,567 and U.S. Pat. No. 6,479,489.

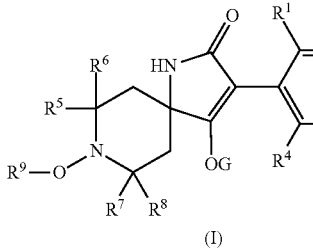

(D)

+

(E)

(C)

Compounds of formula (C) may be prepared by reacting amino acid derivatives of formula (D) with phenylacetyl halides of formula (E), preferably in the presence of base in a suitable solvent by known methods described, for example, in U.S. Pat. No. 6,774,133, U.S. Pat. No. 6,555,567 and U.S. Pat. No. 6,479,489.

Phenylacetyl halides of formula (E), wherein Hal is Cl or Br, are known compounds or can be prepared by known methods as described, for example, in U.S. Pat. No. 6,774,133, U.S. Pat. No. 6,555,567 and U.S. Pat. No. 6,479,489.

Amino acid esters of formula (D), wherein R' is $C_1$-$C_4$alkyl, can be prepared by known methods from amino acids of formula (F). These compounds can be isolated as free amines or amine salts.

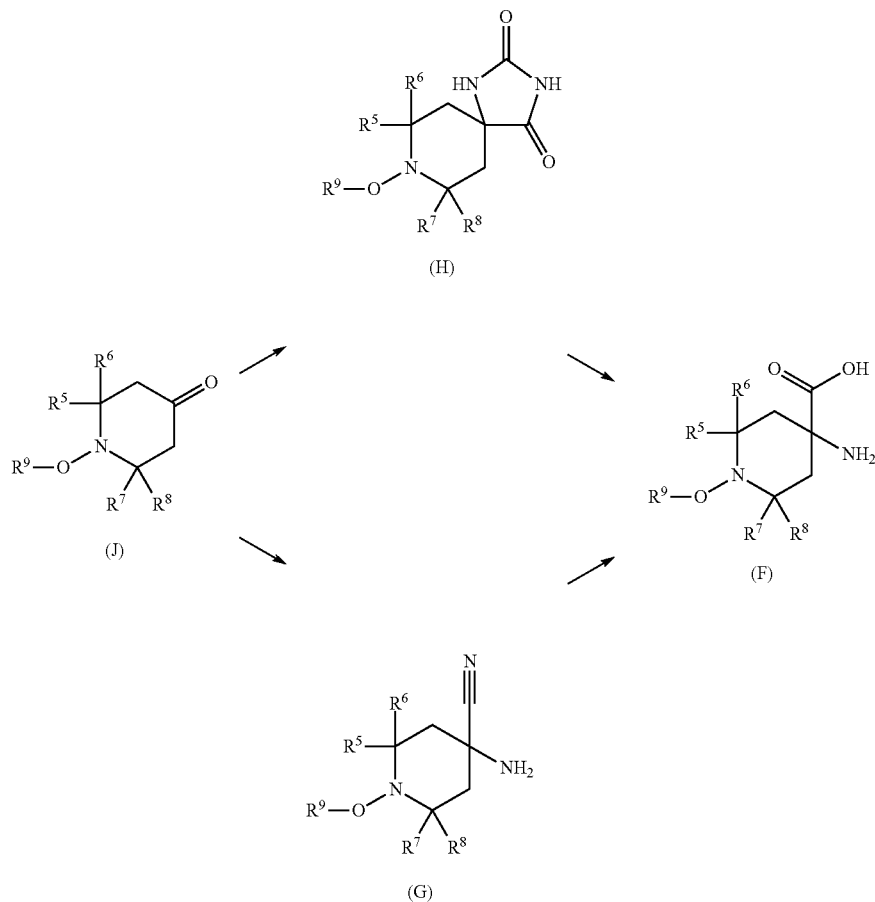

Amino acids of formula (F) can be prepared from ketons of formula (J) by means of Strecker Synthesis via amino nitriles of formula (G).

Alternatively, amino acids of formula (F) can be prepared from ketones of formula (J) by means of Bucherer-Bergs reaction via hydantoins of formula (H).

Compounds of formula J, where $R^5$, $R^6$, $R^7$ and $R^8$ are hydrogen and $R^9$ is $C_{1-4}$ alkyl, $C_{1-4}$ haloalkyl, $C_3$-$C_6$ alkenyl, $C_3$-$C_6$ alkinyl or a benzyl group, are known or can be obtained, for example, according to Journal of Organic Chemistry (1961), 26, 1867-74).

Compounds of formula J, where $R^5$, $R^6$, $R^7$ and $R^8$ are methyl and $R^9$ is a $C_{1-4}$ alkyl or $C_3$-$C_6$ alkenyl, are known or can be obtained in analogy to procedures described, for example, in WO9854174.

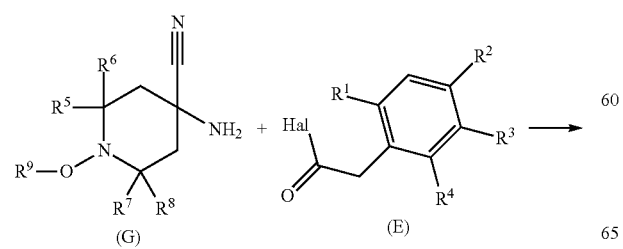

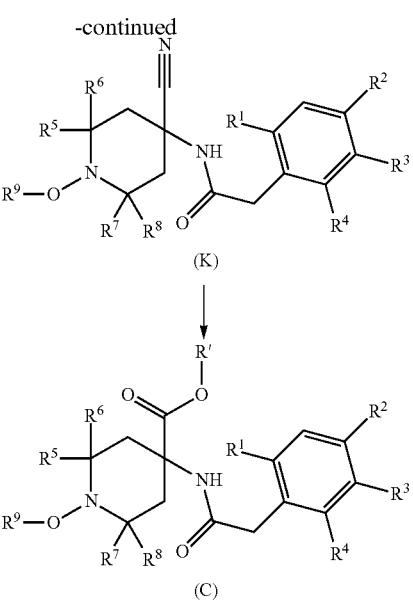

Alternatively, compounds of formula (C) may be prepared by subjecting derivatives of formula (K) to alcoholysis with R'OH, preferably in in acidic media by known methods described, for example, in U.S. Pat. No. 6,774,133, U.S. Pat. No. 6,555,567 and U.S. Pat. No. 6,479,489.

Compounds of formula (K) may be themselves prepared by reacting amino nitriles of formula (G) with phenylacetyl halides of formula (E), preferably in the presence of base in a suitable solvent by known methods described, for example, in U.S. Pat. No. 6,774,133, U.S. Pat. No. 6,555,567 and U.S. Pat. No. 6,479,489.

The starting compounds and intermediates of the reaction schemes are known or can be prepared according to methods known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The inventively used compounds of formula I can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I are generally applied at a rate of 1-2000 g/ha, preferably 1-1000 g/ha and most preferably at 1-500 g/ha.

Preferred formulations have especially the following compositions:

(%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | | | | |
|---|---|---|---|---|
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | | | | |
|---|---|---|---|---|
| | a) | b) | c) | d) |
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | | | | |
|---|---|---|---|---|
| | a) | b) | c) | d) |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | | | |
|---|---|---|---|
| | a) | b) | c) |
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | | | |
|---|---|---|---|
| | a) | b) | c) |
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | | | | |
|---|---|---|---|---|
| | a) | b) | c) | d) |
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | | | |
|---|---|---|---|
| | a) | b) | c) |
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | | | | |
|---|---|---|---|---|
| | a) | b) | c) | d) |
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I used according to the invention can also be used in combination with further herbicides. Preferably, in these mixtures, the compound of the formula I is one of those compounds listed in Tables 1 to 22 below. The following mixtures of the compound of formula I are preferred:

compound of formula I+aclonifen, compound of formula I+amidosulfuron, compound of formula I+aminopyralid, compound of formula I+azimsulfuron, compound of formula I+beflubutamid, compound of formula I+benfluralin, compound of formula I+bensulfuron, compound of formula I+bensulfuron-methyl, compound of formula I+benzobicyclon, compound of formula I+bifenox, compound of formula I+bispyribac, compound of formula I+bispyribac-sodium, compound of formula I+bromoxynil, compound of formula I+butachlor, compound of formula I+butafenacil, compound of formula I+cafenstrole, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+cinosulfuron, compound of formula I+clodinafop, compound of formula I+clodinafop-propargyl, compound of formula I+clomazone, compound of formula I+clomeprop, compound of formula I+clopyralid, compound of formula I+cyclosulfamuron, compound of formula I+cycloxydim, compound of formula I+cyhalofop, compound of formula I+cyhalofop-butyl, compound of formula I+2,4-D, compound of formula I+daimuron, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+esprocarb, compound of formula I+ethoxysulfuron, compound of formula I+fenoxaprop-P, compound of formula I+fenoxaprop-P-ethyl, compound of formula I+fentrazamide, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+glufosinate-ammonium, compound of formula I+glyphosate, compound of formula I+halosulfuron, compound of formula I+halosulfuron-methyl, compound of formula I+imazamethabenz-methyl, compound of formula I+imazamox, compound of formula I+imazosulfuron, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mefenacet, compound of formula I+mesosulfuron, compound of formula I+mesosulfuron-methyl, compound of formula I+mesotrione, compound of formula I+metamifop, compound of formula I+metribuzin, compound of formula I+metsulfuron, compound of formula I+metsulfuron-methyl, compound of formula I+n-methyl glyphosate, compound of formula I+orthosulfamuron, compound of formula I+oryzalin, compound of formula I+oxadiargyl, compound of formula I+oxadiazon, compound of formula I+paraquat dichloride, compound of formula I+pendimethalin, compound of formula I+penoxsulam, compound of formula I+picolinafen, compound of formula I+pinoxaden, compound of formula I+pretilachlor, compound of formula I+prodiamine, compound of formula I+profoxydim, compound of formula I+propanil, compound of formula I+propoxycarbazone, compound of formula I+propoxycarbazone-sodium, compound of formula I+prosulfocarb, compound of formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyridate, compound of formula I+pyriftalid, compound of formula I+pyriminobac-methyl, compound of formula I+pyrimisulfan, compound of formula I+pyroxasulfone (KIN-485), compound of formula I+pyroxsulam, compound of formula I+quinclorac, compound of formula I+sulfosulfuron, compound of formula I+tefuryltrione, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl, compound of formula I+tritosulfuron, The following mixtures of the compound of formula I are especially preferred:

compound of formula I+amidosulfuron, compound of formula I+aminopyralid, compound of formula I+azimsulfuron, compound of formula I+beflubutamid, compound of formula I+bensulfuron, compound of formula I+bensulfuron-methyl, compound of formula I+benzobicyclon, compound of formula I+bispyribac, compound of formula I+bispyribac-sodium, compound of formula I+bromoxynil, compound of formula I+carfentrazone, compound of formula I+carfentrazone-ethyl, compound of formula I+chlorotoluron, compound of formula I+chlorsulfuron, compound of formula I+clodinafop, compound of formula I+clodinafop-propargyl, compound of formula I+clomazone, compound of formula I+clomeprop, compound of formula I+clopyralid, compound of formula I+cycloxydim, compound of formula I+cyhalofop, compound of formula I+cyhalofop-butyl, compound of formula I+2,4-D, compound of formula I+daimuron, compound of formula I+dicamba, compound of formula I+difenzoquat, compound of formula I+difenzoquat metilsulfate, compound of formula I+diflufenican, compound of formula I+esprocarb, compound of formula I+ethoxysulfuron, compound of formula I+fenoxaprop-P, compound of formula I+fenoxaprop-P-ethyl, compound of formula I+fentrazamide, compound of formula I+florasulam, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluoroxypyr, compound of formula I+flurtamone, compound of formula I+halosulfuron, compound of formula I+halosulfuron-methyl, compound of formula I+imazosulfuron, compound of formula I+iodosulfuron, compound of formula I+iodosulfuron-methyl-sodium, compound of formula I+MCPA, compound of formula I+mefenacet, compound of formula I+mesosulfuron, compound of formula I+mesosulfuron-methyl, compound of formula I+metsulfuron, compound of formula I+metsulfuron-methyl, compound of formula I+orthosulfamuron, compound of formula I+oxadiargyl, compound of formula I+oxadiazon, compound of formula I+pendimethalin, compound of formula I+penoxsulam, compound of formula I+picolinafen, compound of formula I+pinoxaden, compound of formula I+pretilachlor, compound of formula I+prosulfocarb, compound of formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyriftalid, compound of formula I+pyriminobac-methyl, compound of formula I+pyrimisulfan, compound of formula I+pyroxasulfone (KIN-485), compound of formula I+pyroxsulam, compound of formula I+quinclorac, compound of formula I+sulfosulfuron, compound of formula I+tefuryltrione, compound of formula I+thifensulfuron, compound of formula I+thifensulfuron-methyl, compound of formula I+tralkoxydim, compound of formula I+triasulfuron, compound of formula I+tribenuron, compound of formula I+tribenuron-methyl, compound of formula I+trifluralin, compound of formula I+trinexapac-ethyl, compound of formula I+tritosulfuron, The mixing partners for the compound of formula I may also be in the form of esters or salts, as mentioned e.g. in The Pesticide Manual, 12th Edition (BCPC) 2000.

The compounds of formula I used according to the invention can also be used in combination with safeners. Preferably, in these mixtures, the compound of the formula I is one of those compounds listed in Tables 1 to 22 below. The following mixtures with safeners, especially, come into consideration:

compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

It is preferred to apply the other herbicide together with one of the safeners mentioned above.

The following Examples illustrate the invention further but do not limit the invention.

PREPARATION EXAMPLES

Example 1

Preparation of carbonic acid 3-(2,5-dimethyl-phenyl)-8-methoxy-2-oxo-1,8-diaza-spiro[4.5]dec-3-en-4-yl ester methyl ester

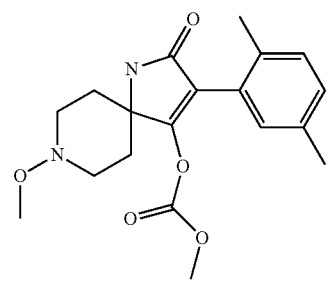 [SMILES: COC(=O)OC1=C(c2cc(C)ccc2C)C(=O)NC12CCN(OC)CC2]

Step 1:

Preparation of
4-amino-1-methoxy-piperidine-4-carbonitrile

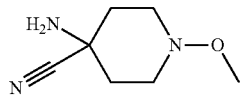

To 10 g of N-methoxy-4-piperidone (*J. Org. Chem.* 1961, 26, 1867-74) in 240 ml ammoniumhydroxide 25% in water there are added 6.2 g of ammoniumchloride and 4.6 g of sodium cyanide. After stirring for 18 h at 25° C. the reaction mixture is diluted with 200 ml water and extracted with ethyl acetate. The organic phase is separated, dried over sodium sulphate, filtered and evaporated. 8.25 g of 4-amino-1-methoxy-piperidine-4-carbonitrile is obtained as light brow oil, which is used without further purification in the next step.

$^1$H-NMR (CDCl$_3$): ☐ 1.61-2.22 (br signals, total 6H), 2.61-3.43 (br signals, total 4H), 3.51 (s, 3H).

Step 2:

Preparation of
4-amino-1-methoxy-piperidine-4-carboxylic acid as
hydrochloride salt

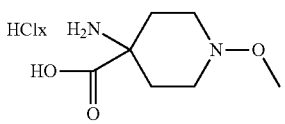

A mixture of 8.25 g of 4-amino-1-methoxy-piperidine-4-carbonitrile and 30 ml hydrochloric acid 32% is heated to 100° C. After 16 h the reacton mixture is evaporated. The solid residue is suspended in ethanol, filtered and dried to obtain 12.5 g of 4-Amino-1-methoxy-piperidine-4-carboxylic acid as hydrochloride salt.

Step 3:

Preparation of
4-amino-1-methoxy-piperidine-4-carboxylic acid
methyl ester hydrochloride

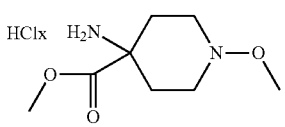

25.7 g of thionylchloride are added at a temperature of 0-10° C. within 40 minutes to a suspension of 12.5 g of 4-amino-1-methoxy-piperidine-4-carboxylic acid in 100 ml of methanol. The reaction mixture is then heated up to 60° C. for 48 h. After cooling to 20° C., the solids are filtered and the filtrate is evaporated to give 13.2 g of 4-amino-1-methoxy-piperidine-4-carboxylic acid methyl ester hydrochloride as brown cristalline solid.

$^1$H-NMR (CDCl$_3$, free base): ☐ 1.40-1.72 (br signals, total 2H), 1.58 (s, 2H), 2.02-2.37 (br signals, total 2H), 2.58-2.90 (br signals, total 2H), 3.04-3.32 (br signals, total 2H), 3.52 (s, 3H), 3.73 (s, 3H).

LC-MS (EI, ES+): 189 (M+H)$^+$

Step 4:

Preparation of methyl 4-[2-(2,5-dimethyl-phenyl)
acetylamino]-1-methoxy-piperidine-4-carboxylate

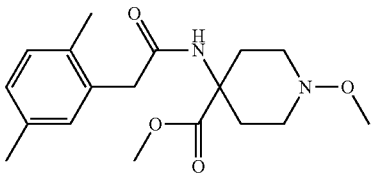 [SMILES: COC(=O)C1(NC(=O)Cc2cc(C)ccc2C)CCN(OC)CC1]

To 5.4 g of potassium carbonate and 2 g of 4-Amino-1-methoxy-piperidine-4-carboxylic acid methyl ester hydrochloride in 10 ml of acetonitrile, 1.94 g of (2,5-dimethyl-phenyl)-acetyl chloride in 5 ml of acetonitrile are added at a temperature of 0-5° C. After stirring for 22 h at room temperature the reaction mixture is poored on cold water and extracted with ethyl-acetate. The organic phase is dried over sodium sulfate, filtered and evaporated to yield 2.13 g of methyl 4-[2-(2,5-dimethyl-phenyl)acetylamino]-1-methoxy-piperidine-4-carboxylate as beige cristalline solid. $^1$H-NMR (CDCl$_3$): ☐ 1.95-2.30 (br signals, total 4H), 2.27 (s, 3H), 2.33 (s, 3H), 2.77-3.23 (br signals, total 4H), 3.48 (s, 3H), 3.54 (s, 2H), 3.71 (s, 3H), 5.40 (br s, 1H), 7.02 (s, 1H), 7.04 (d, 1H), 7.11 (d, 1H).

LC-MS (EI, ES+): 335 (M+H)$^+$

Step 5:

Preparation of 3-(2,5-dimethyl-phenyl)-4-hydroxy-8-
methoxy-1,8-diaza-spiro[4.5]dec-3-en-2-one To 0.82 g of sodium methylate in 20 ml of DMF a solution of 4-[2-(2,5-dimethyl-phenyl)-acetylamino]-1-methoxy-piperidine-4-carboxylic acid methyl ester in 10 ml DMF is added at a temperature of 60° C. After stirring for 3 h at 60° C. the reaction mixture is evaporated. The residue is diluted with 10 ml water, neutralized with 10% hydrochloric acid and extracted with ethyl acetate. The organic phase is dried over sodium sulfate, filtered and evaporated to give 3-(2,5-dimethyl-phenyl)-4-hydroxy-8-methoxy-1,8-diaza-spiro[4.5] dec-3-en-2-one as a light brown resin. This material is triturated with diethyl ether/hexane, filtered and dried to afford a solid, mp: 176-177° C.

LC-MS (EI, ES+): 303 (M+H)$^+$

Step 6:

Preparation of carbonic acid 3-(2,5-dimethyl-phe-
nyl)-8-methoxy-2-oxo-1,8-diaza-spiro[4.5]dec-3-en-
4-yl ester methyl ester

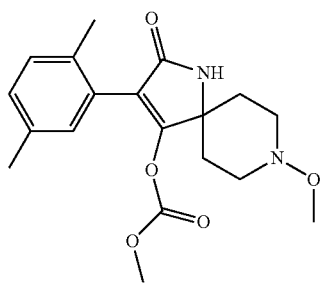 [SMILES: COC(=O)OC1=C(c2cc(C)ccc2C)C(=O)NC12CCN(OC)CC2]

To a solution of 200 mg of 3-(2,5-dimethyl-phenyl)-4-hydroxy-8-methoxy-1,8-diaza-spiro[4.5]dec-3-en-2-one and 0.14 ml of ethyl diisopropyl amine in 2 ml of chlorobenzene is added a solution of 66 mg of methyl chloroformate in 0.5 ml of chlorobenzene at 50° C. After stirring for 1 hour at 50° C., the reaction mixture is cooled to room temperature, diluted with 5 ml of chlorobenzene and washed with cold 5% aqueous sodium hydroxide and water. The organic phase is separated, dried over sodium sulfate, filtered and evaporated. The residue is purified by flash chromatography on silica gel. Yield: 120 mg of carbonic acid 3-(2,5-dimethyl-phenyl)-8-methoxy-2-oxo-1,8-diaza-spiro[4.5]dec-3-en-4-yl ester methyl ester. This material is triturated with ethyl acetate/hexane, filtered and dried to afford a solid, mp: 186-188° C.

$^1$H-NMR (CDCl$_3$): ☐ 1.73 (m, 2H), 2.21 (s, 3H), 2.24 (m, 2H), 2.30 (s, 3H), 2.52 (m, 2H), 3.46 (m, 2H), 3.56 (br s, 3H), 3.63 (s, 3H), 6.78 (br s, 1H), 6.98 (s, 1H), 7.05 (d, 1H), 7.11 (d, 1H).

LC-MS (EI, ES+): 361 (M+H)$^+$

Example 2

Preparation of 2,2-dimethyl-propionic acid 8-ethoxy-2-oxo-3-(2,4,6-trimethyl-phenyl)-1,8-diaza-spiro[4.5]dec-3-en-4-yl ester

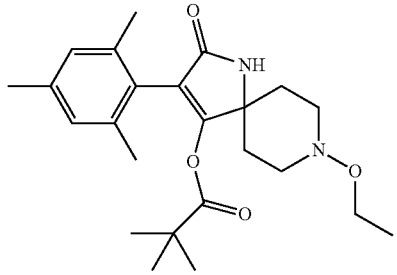 [SMILES: CCON1CCC2(CC1)NC(=O)C(c1c(C)cc(C)cc1C)=C2OC(=O)C(C)(C)C]

Step 1:

Preparation of 4-amino-1-ethoxy-piperidine-4-carbonitrile

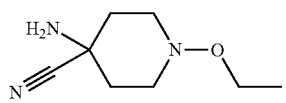

4-Amino-1-ethoxy-piperidine-4-carbonitrile is prepared analogously to the synthesis of 4-amino-1-methoxy-piperidine-4-carbonitrile (preparation example 1, Step 1) starting from N-ethoxy-4-piperidone (Journal of Organic Chemistry (1961), 26, 1867-74).

$^1$H-NMR (d$_6$-DMSO, 88° C.): ☐ 1.08 (t, 3H), 1.71 (m, 2H), 1.93 (m, 2H), 2.38 (br s, 2H), 2.67 (m, 2H), 3.09 (m, 2H), 3.63 (q, 2H).

LC-MS (EI, ES+): 170 (M+H)$^+$

Step 2:

Preparation of N-(4-cyano-1-ethoxy-piperidin-4-yl)-2-(2,4,6-trimethyl-phenyl)acetamide

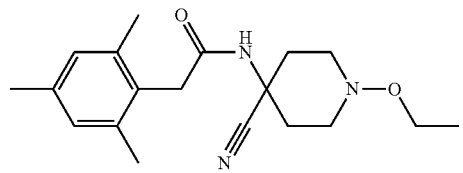 [SMILES: CCON1CCC(C#N)(NC(=O)Cc2c(C)cc(C)cc2C)CC1]

3.0 g of (2,4,6-trimethyl-phenyl)-acetyl chloride and 10 g of potassium carbonate in 90 ml of acetonitrile are treated at 0° C. with a solution of 3.6 g of 4-amino-1-ethoxy-piperidine-4-carbonitrile in 30 ml of acetonitrile. After stirring for 18 hours at room temperature the reaction mixture is poured into 100 ml of ice water and extracted with ethyl acetate. The organic phase is washed with brine and concentrated. Chromatography (heptane/ethyl acetate 5:1) yielded 4.5 g of N-(4-cyano-1-ethoxy-piperidin-4-yl)-2-(2,4,6-trimethyl-phenyl)-acetamide as a solid, mp: 194-195° C. LC-MS (EI, ES+): 330 (M+H)$^+$ Step 3:

Preparation of 1-ethoxy-4-[2-(2,4,6-trimethyl-phenyl)-acetylamino]-piperidine-4-carboxylic acid methyl ester

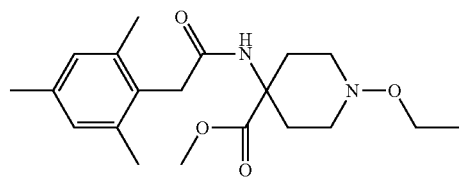 [SMILES: CCON1CCC(NC(=O)Cc2c(C)cc(C)cc2C)(C(=O)OC)CC1]

1.4 ml of concentrated sulfuric acid is slowly added to a solution of 4.3 g of N-(4-cyano-1-ethoxy-piperidin-4-yl)-2-(2,4,6-trimethyl-phenyl)-acetamide in 11 ml of methanol. After stirring 20 hours under reflux, the reaction mixture is allowed to cool down to room temperature and diluted with ice water. Sodium carbonate is added and the aqueous phase is extracted with ethyl acetate. The organic phase is dried over sodium sulfate, filtered and concentrated. Chromatography (dichloromethane+1% of ethanol) gave 3.2 g of 1-ethoxy-4-[2-(2,4,6-trimethyl-phenyl)-acetylamino]-piperidine-4-carboxylic acid methyl ester as a solid, mp: 131-132° C.

LC-MS (EI, ES+): 363 (M+H)$^+$

Step 4:

Preparation of 8-ethoxy-4-hydroxy-3-(2,4,6-trimethyl-phenyl)-1,8-diaza-spiro[4.5]dec-3-en-2-one

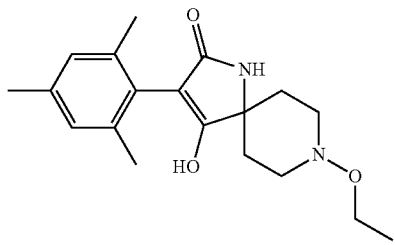 [SMILES: CCON1CCC2(CC1)NC(=O)C(c1c(C)cc(C)cc1C)=C2O]

To a solution of 2.3 g of 1-ethoxy-4-[2-(2,4,6-trimethyl-phenyl)-acetylamino]-piperidine-4-carboxylic acid methyl ester in 26 ml of dimethylformamide is added 3 g of sodium methoxide. The reaction mixture is heated to 65° C. and stirred for 5 hours. The reaction mixture is poured into brine, neutralized and extracted with ethyl acetate. The organic phase is washed with brine, dried with sodium sulfate, filtered and concentrated. The residue is subjected to column chromatography (heptane/ethyl acetate 2:1) to yield 510 mg of 8-ethoxy-4-hydroxy-3-(2,4,6-trimethyl-phenyl)-1,8-diaza-spiro[4.5]dec-3-en-2-one as a solid, mp: >250° C.

LC-MS (EI, ES+): 331 (M+H)$^+$

Step 5:

Preparation of 2,2-dimethyl-propionic acid 8-ethoxy-2-oxo-3-(2,4,6-trimethyl-phenyl)-1,8-diaza-spiro[4.5]dec-3-en-4-yl ester

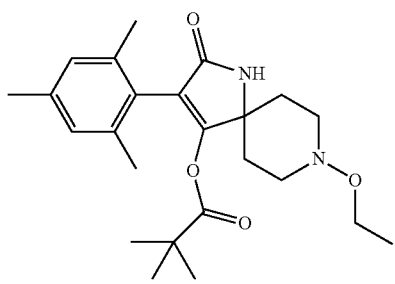 [SMILES: CCON1CCC2(CC1)NC(=O)C(c1c(C)cc(C)cc1C)=C2OC(=O)C(C)(C)C]

To 143 mg of 8-ethoxy-4-hydroxy-3-(2,4,6-trimethyl-phenyl)-1,8-diaza-spiro[4.5]dec-3-en-2-one in 1 ml of tetrahydrofuran are added 36 □l of pyridine and 53 □l of pivaloyl chloride. After stirring at room temperature for 20 hours, water and ethyl acetate are added and the phases separated. The aqueous phase is extracted with ethyl acetate, the combined organic phases dried with sodium sulfate, filtered and concentrated. Chromatography (heptane/ethyl acetate 2:1) yielded 117 mg of 2,2-dimethyl-propionic acid 8-ethoxy-2-oxo-3-(2,4,6-trimethyl-phenyl)-1,8-diaza-spiro[4.5]dec-3-en-4-yl ester as a solid, mp: 230-231° C.

$^1$H-NMR (CDCl$_3$): □ 1.05 (s, 9H), 1.18 (t, 3H), 1.70 (m, 2H), 2.12 (m, 2H), 2.14 (s, 6H), 2.22 (s, 3H), 2.51 (m, 2H), 3.38 (m, 2H), 3.75 (q, 2H), 6.42 (br s, 1H), 6.81 (s, 2H).

LC-MS (EI, ES+): 415 (M+H)$^+$

Example 3

Preparation of 3-(5-cyclopropyl-2,4-dimethyl-phenyl)-4-hydroxy-8-methoxy-1,8-diaza-spiro[4.5]dec-3-en-2-one

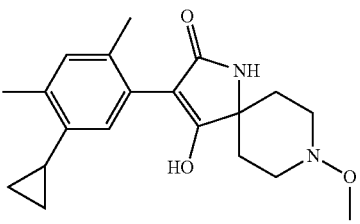

Step 1:

Preparation of (5-cyclopropyl-2,4-dimethyl-phenyl)acetic acid methyl ester

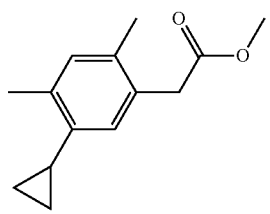

To a solution of 6.0 g of (5-bromo-2,4-dimethyl-phenyl)-acetic acid methyl ester (WO99/48869) in 100 ml of toluene is added 2.2 g of cyclopropylboronic acid and 20 g of potassium phosphate tribasic trihydrate at room temperature. The reaction mixture is stirred for 5 minutes under nitrogen atmosphere, followed by further addition of 1.2 g of tetrakis(triphenylphosphine)palladium(0). After heating and stirring for 16 hours at 110° C., the reaction mixture is filtered, the solvent removed in vacuo and the residue is subjected to silica gel chromatography (isohexane/diethyl ether 2:1) to yield 2.5 g of (5-cyclopropyl-2,4-dimethyl-phenyl)-acetic acid methyl ester.

Step 2:

Preparation of (5-cyclopropyl-2,4-dimethyl-phenyl)acetic acid

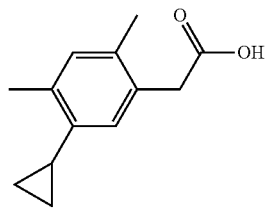

2.5 g of (5-cyclopropyl-2,4-dimethyl-phenyl)-acetic acid methyl ester in 30 ml of methanol is kept at ice bath temperature and treated with 0.5 g of sodium hydroxide in 5 portions. The reaction mixture is stirred at room temperature for 1.5 hours. The solvent is removed in vacuo, the residue poured into water and extracted with diethyl ether. The combined organic phases are dried with sodium sulfate, filtered and concentrated to afford 2.3 g of (5-cyclopropyl-2,4-dimethyl-phenyl)-acetic acid.

Step 3:

Preparation of (5-cyclopropyl-2,4-dimethyl-phenyl)-acetyl chloride

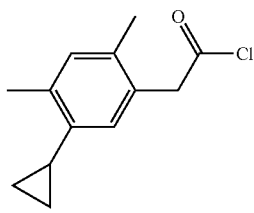

2.3 g of (5-cyclopropyl-2,4-dimethyl-phenyl)-acetic acid in 20 ml of dichloromethane are treated with 2.1 g of oxalyl chloride and a catalytic amount of dimethylformamide. The reaction mixture is stirred at room temperature for 2 hours. The solvent is removed in vacuo and the crude residue of (5-cyclopropyl-2,4-dimethyl-phenyl)-acetyl chloride (2.5 g) is used for the next step.

Step 4:

Preparation of 4-[2-(5-cyclopropyl-2,4-dimethyl-phenyl)acetylamino]-1-methoxy-piperidine-4-carboxylic acid methyl ester

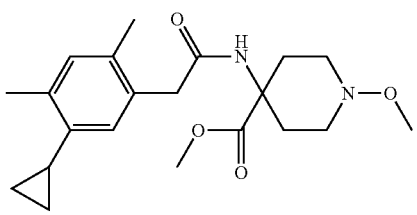

To 4 g of potassium carbonate and 2.5 g of 4-amino-1-methoxy-piperidine-4-carboxylic acid methyl ester hydrochloride (preparation example P1, step P1.3) in 10 ml of acetonitrile is added at 0-5° C. a solution of 2.1 g of crude (5-cyclopropyl-2,4-dimethyl-phenyl)-acetyl chloride in 5 ml of acetonitrile. After stirring for 18 hours at room temperature, the solvent is removed in vacuo and the crude residue of 4-[2-(5-cyclopropyl-2,4-dimethyl-phenyl)-acetylamino]-1-methoxy-piperidine-4-carboxylic acid methyl ester (3.2 g) is used without further purification in the next step.

Step 5:

Preparation of 3-(5-cyclopropyl-2,4-dimethyl-phenyl)-4-hydroxy-8-methoxy-1,8-diaza-spiro[4.5]dec-3-en-2-one

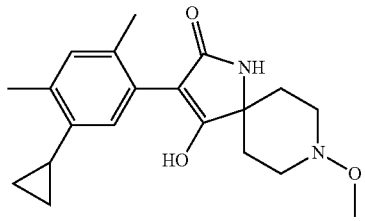

To 1.3 g of sodium methoxide in 10 ml of dimethylformamide is added a solution of 3.2 g of crude 4-[2-(5-cyclopropyl-2,4-dimethyl-phenyl)-acetylamino]-1-methoxy-piperidine-4-carboxylic acid methyl ester in 10 ml of dimethylformamide and the reaction mixture is heated to 65° C. for 2 hours. The mixture is poured into ice water, extracted with dichloromethane, the combined organic phases dried with sodium sulfate, filtered and concentrated. The residue is subjected to column chromatography (dichloromethane/methanol 95:5) to yield 700 mg of 3-(5-cyclopropyl-2,4-dimethyl-phenyl)-4-hydroxy-8-methoxy-1,8-diaza-spiro[4.5]dec-3-en-2-one as a wax.

LC-MS (EI, ES+): 343 (M+H)$^+$

Example 4

Preparation of 2,2-dimethyl-propionic acid 3-(4'-chloro-6-fluoro-4-methyl-biphenyl-3-yl)-8-methoxy-2-oxo-1,8-diaza-spiro[4.5]dec-3-en-4-yl ester

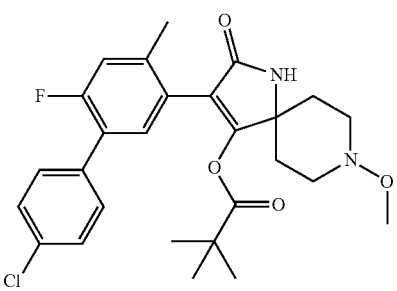 [SMILES: CON1CCC2(CC1)NC(=O)C(c1cc(-c3ccc(Cl)cc3)c(F)cc1C)=C2OC(=O)C(C)(C)C]

Step 1:

Preparation of 1-bromo-2-fluoro-4-methyl-5-(2,2,2-trichloro-ethyl)-benzene

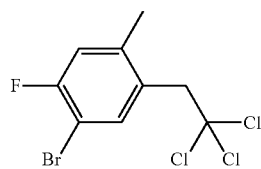

To a solution of vinylidene chloride (127 ml), tert-butyl nitrite (19 ml) and copper(II)chloride (18.4 g) in acetonitrile (150 ml) is added a solution of 5-bromo-4-fluoro-2-methyl-phenylamine (Bioorganic & Medicinal Chemistry Letters (2006), 16(2), 457-460) (21.5 g) in acetonitrile (100 ml) dropwise below 20° C. The reaction mixture is stirred at room temperature for 48 hours, poured on diluted HCl and extracted with tert-butyl methyl ether (3×). The combined organic layers are washed with brine, dried over sodium sulfate and concentrated. The residue is purified by chromatography on silica gel (ethyl acetate/cyclohexane 1:4). Yield: 29.20 g of 1-bromo-2-fluoro-4-methyl-5-(2,2,2-trichloro-ethyl)-benzene as an oil.

$^1$H-NMR (CDCl$_3$): ☐ 2.42 (s, 3H), 3.93 (s, 2H), 7.00 (d, $^3$J (H, F)=9.2 Hz, 1H), 7.69 (d, $^4$J (H, F)=7.0 Hz, 1H).

Step 2:

Preparation of (5-bromo-4-fluoro-2-methyl-phenyl)-acetic acid methyl ester

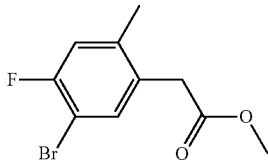

To a solution of 1-bromo-2-fluoro-4-methyl-5-(2,2,2-trichloro-ethyl)-benzene (29.2 g) in methanol (100 ml) is added a sodium methoxide solution (30% in methanol, 78.2 ml) dropwise. The reaction mixture is stirred at reflux for 24 hours, cooled to 5° C. and treated with concentrated sulfuric acid (13.2 ml) dropwise. After further warming to reflux for 21 hours, the mixture is concentrated and the residue diluted with water/ethyl acetate. The aqueous layer is extracted with ethyl acetate, the combined organic layers are washed with brine, dried over sodium sulfate and concentrated. The residue is purified by chromatography on silica gel (ethyl acetate/cyclohexane 1:3). Yield: 18.76 g of (5-bromo-4-fluoro-2-methyl-phenyl)-acetic acid methyl ester as an oil.

$^1$H-NMR (CDCl$_3$): ☐ 2.24 (s, 3H), 3.56 (s, 2H), 3.69 (s, 3H), 6.93 (d, $^3$J (H, F)=9.3 Hz, 1H), 7.35 (d, $^4$J (H, F)=7.0 Hz, 1H).

Step 3:

Preparation of (5-bromo-4-fluoro-2-methyl-phenyl)-acetic acid

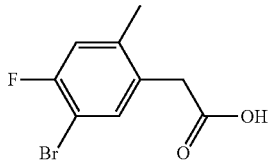

To a solution of (5-bromo-4-fluoro-2-methyl-phenyl)-acetic acid methyl ester (10.3 g) in methanol (50 ml) is added 1N aqueous sodium hydroxide (47.4 ml) and the reaction mixture is stirred at room temperature for 18 hours. The mixture is concentrated, the residue treated with 1N hydrochloric acid, the resulting precipitate filtered off, washed with ice-water and dried. Yield: 8.60 g of (5-bromo-4-fluoro-2-methyl-phenyl)-acetic acid as a solid, mp: 100-101° C.

$^1$H-NMR (CDCl$_3$): ☐ 2.26 (s, 3H), 3.60 (s, 2H), 6.95 (d, $^3$J (H, F)=9.3 Hz, 1H), 7.36 (d, $^4$J (H, F)=7.0 Hz, 1H), 8.6 (br s, 1H).

Step 4:

Preparation of 4-[2-(5-bromo-4-fluoro-2-methyl-phenyl)-acetylamino]-1-methoxy-piperidine-4-carboxylic acid methyl ester

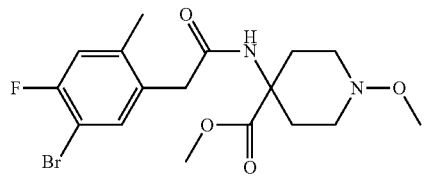 [SMILES: COC(=O)C1(NC(=O)Cc2cc(Br)c(F)cc2C)CCN(OC)CC1]

A suspension of (5-bromo-4-fluoro-2-methyl-phenyl)-acetic acid (8.0 g) and 1,1'-carbonyldiimidazole (5.8 g) in tetrahydrofuran (150 ml) is heated at reflux for 30 minutes. Upon cooling to room temperature, triethylamine (9.0 ml) and 4-amino-1-methoxy-piperidine-4-carboxylic acid methyl ester hydrochloride salt (13.8 g) are added and warming at reflux is continued for 3 hours. The cold reaction mixture is poured on water/ethyl acetate, the layers separated, the organic phase washed with brine, dried over sodium sulfate and concentrated. The residue is solubilised in ethyl acetate/cyclohexane 3:1 and purified by filtration on alumina. Yield: 6.83 g of 4-[2-(5-bromo-4-fluoro-2-methyl-phenyl)-acetylamino]-1-methoxy-piperidine-4-carboxylic acid methyl ester as a solid, mp: 192-193° C.

$^1$H-NMR (CDCl$_3$): ☐ 2.04-2.54 (br signals, total 4H), 2.26 (s, 3H), 2.79-3.27 (br signals, total 4H), 3.49 (br s, 5H), 3.71 (s, 3H), 5.40 (br s, 1H), 6.99 (d, $^3$J (H, F)=9.3 Hz, 1H), 7.38 (d, $^4$J (H, F)=6.9 Hz, 1H).

MS (FIMS-EI, ES+): 417/419 (M+H)$^+$

Step 5:

Preparation of 3-(5-Bromo-4-fluoro-2-methyl-phenyl)-4-hydroxy-8-methoxy-1,8-diaza-spiro[4.5]dec-3-en-2-one

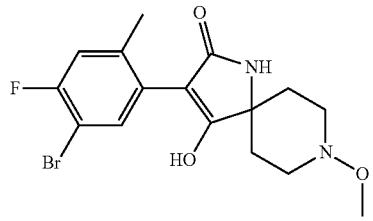 [SMILES: CON1CCC2(CC1)NC(=O)C(c1cc(Br)c(F)cc1C)=C2O]

To a solution of 4-[2-(5-bromo-4-fluoro-2-methyl-phenyl)-acetylamino]-1-methoxy-piperidine-4-carboxylic acid methyl ester (6.0 g) in dimethylformamide (20 ml) at 100° C. is added potassium tert-butoxide (3.23 g) and stirring continued at 100° C. for 10 minutes. The reaction mixture is quenched at room temperature by addition of acetic acid (1.64 ml), diluted with water (20 ml) and extracted with tert-butyl methyl ether (3×). The combined organic layers are washed with brine, dried over sodium sulfate and concentrated. The residue is triturated with acetonitrile, filtered and dried. Yield: 3.69 g of 3-(5-bromo-4-fluoro-2-methyl-phenyl)-4-hydroxy-8-methoxy-1,8-diaza-spiro[4.5]dec-3-en-2-one as a solid, mp: 229-230° C.

$^1$H-NMR (d$_6$-DMSO): ☐ 1.45 (m, 2H), 2.09 (s, 3H), 2.15 (m, 2H), 2.62 (m, 2H), 3.25 (m, 2H), 3.42 (s, 3H), 6.93 (d, $^3$J (H, F)=9.8 Hz, 1H), 7.27 (d, $^4$J (H, F)=7.3 Hz, 1H), 7.92 (br s, 1H), 10.64 (br s, 1H).

MS (FIMS-EI, ES−): 383/385 (M−H)$^-$

Step 6:

Preparation of 3-(4'-Chloro-6-fluoro-4-methyl-biphenyl-3-yl)-4-hydroxy-8-methoxy-1,8-diaza-spiro[4.5]dec-3-en-2-one

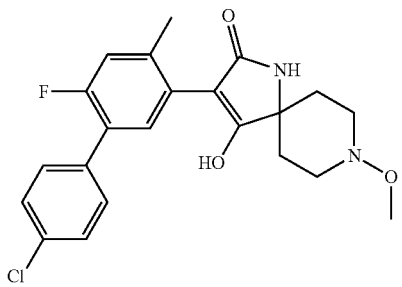 [SMILES: CON1CCC2(CC1)NC(=O)C(c1cc(-c3ccc(Cl)cc3)c(F)cc1C)=C2O]

To a suspension of 3-(5-bromo-4-fluoro-2-methyl-phenyl)-4-hydroxy-8-methoxy-1,8-diaza-spiro[4.5]dec-3-en-2-one (230 mg) in dimethoxyethane (10 ml) under nitrogen atmosphere is added tetrakis(triphenylphosphine)palladium (0) (35 mg) and the mixture stirred at room temperature for 15 minutes. After further addition of water (2 ml), 4-chlorophenylboronic acid (112 mg) and sodium carbonate (250 mg), the mixture is heated at reflux for 8 hours. The reaction mixture is acidified at room temperature with 1N hydrochloric acid and extracted with ethyl acetate (3×). The combined organic layers are washed with brine, dried over sodium sulfate and concentrated. The residue is purified by chromatography on silica gel (ethyl acetate/cyclohexane 5:1). Yield: 170 mg of 3-(4'-chloro-6-fluoro-4-methyl-biphenyl-3-yl)-4-hydroxy-8-methoxy-1,8-diaza-spiro[4.5]dec-3-en-2-one (compound C24) as a solid.

MS (FIMS-EI, ES+): 417/419 (M+H)$^+$; MS (FIMS-EI, ES−): 415/417 (M−H)$^-$

Step 7:

Preparation of 2,2-dimethyl-propionic acid 3-(4'-chloro-6-fluoro-4-methyl-biphenyl-3-yl)-8-methoxy-2-oxo-1,8-diaza-spiro[4.5]dec-3-en-4-yl ester

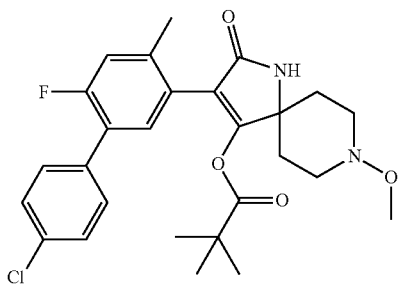 [SMILES: CON1CCC2(CC1)NC(=O)C(c1cc(-c3ccc(Cl)cc3)c(F)cc1C)=C2OC(=O)C(C)(C)C]

To a solution of 3-(4'-chloro-6-fluoro-4-methyl-biphenyl-3-yl)-4-hydroxy-8-methoxy-1,8-diaza-spiro[4.5]dec-3-en-2-one (170 mg) and pivaloyl chloride (98 mg) in acetonitrile (5 ml) is added pyridine (64 mg) and the reaction mixture stirred at room temperature for 8 hours. The mixture is poured on diluted HCl and extracted with ethyl acetate (3×). The combined organic layers are washed with brine, dried over sodium sulfate and concentrated. The residue is triturated with heptane, filtered and dried. Yield: 100 mg of 2,2-dimethyl-propionic acid 3-(4'-chloro-6-fluoro-4-methyl-biphenyl-3-yl)-8-methoxy-2-oxo-1,8-diaza-spiro[4.5]dec-3-en-4-yl ester as a solid, mp: 150-151° C.

$^1$H-NMR (CDCl$_3$): ☐ 1.09 (s, 9H), 1.72 (m, 2H), 2.10 (m, 2H), 2.29 (s, 3H), 2.49 (m, 2H), 3.44 (m, 2H), 3.55 (s, 3H), 6.59 (s, 1H), 7.02 (d, $^3$J (H, F)=11.5 Hz, 1H), 7.10 (d, $^4$J (H, F)=8.0 Hz, 1H), 7.36 (d, 2H), 7.41 (d, 2H).

Example 5

Preparation of 3-(2,5-dimethyl-phenyl)-4-ethoxymethoxy-8-methoxy-1,8-diaza-spiro[4.5]dec-3-en-2-one

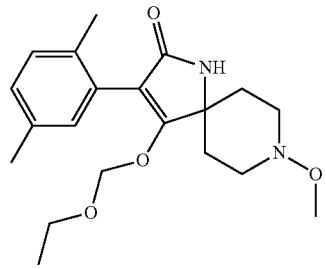 [SMILES: CCOCOC1=C(c2cc(C)ccc2C)C(=O)NC12CCN(OC)CC2]

To 250 mg of 3-(2,5-dimethyl-phenyl)-4-hydroxy-8-methoxy-1,8-diaza-spiro[4.5]dec-3-en-2-one in 2.5 ml of tetrahydrofuran are added 160 ☐l of Hünig's base and 85 ☐l of chloromethyl ethyl ether. After stirring for 20 hours at room temperature, water and ethyl acetate are added and the layers are separated. The aqueous phase is extracted with ethyl acetate, the combined organic phases dried with sodium sulfate, filtered and concentrated. Chromatography (heptane/acetone 4:1) yielded 72 mg of 3-(2,5-dimethyl-phenyl)-4-ethoxymethoxy-8-methoxy-1,8-diaza-spiro[4.5]dec-3-en-2-one as a solid, mp:150-152° C.

$^1$H-NMR (CDCl$_3$): ☐ 1.15 (t, 3H), 1.65 (m, 2H), 2.16 (s, 3H), 2.28 (s, 3H), 2.31 (m, 2H), 2.45 (m, 2H), 3.46 (m, 2H), 3.56 (s, 3H), 3.58 (q, 2H), 4.80 (s, 2H), 6.05 (br s, 1H), 6.97 (s, 1H), 7.03 (d, 1H), 7.08 (d, 1H).

LC-MS (EI, ES+): 361 (M+H)$^+$

Additional compounds in Table T1 and P1 below are prepared by similar methods using appropriate starting materials.

TABLE T1

| Compound Number | Structure | physical data |
|---|---|---|
| T1 | 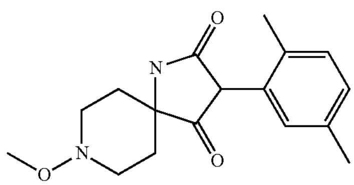 | Mp: 176-177° C. |
| T2 | 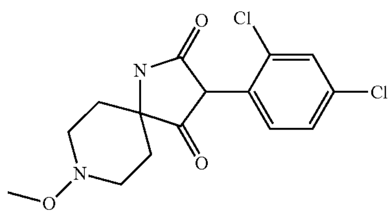 [SMILES: CON1CCC2(CC1)NC(=O)C(c1ccc(Cl)cc1Cl)C2=O] | Mp: 221-223° C. |
| T3 | 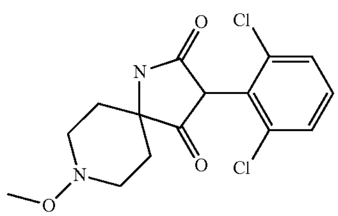 [SMILES: CON1CCC2(CC1)NC(=O)C(c1c(Cl)cccc1Cl)C2=O] | Mp: 257-260° C. |
| T4 | 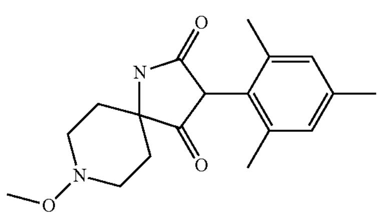 | Mp: 253-255° C. |
| T5 | 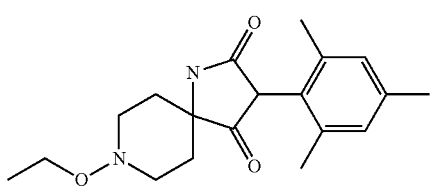 [SMILES: CCON1CCC2(CC1)NC(=O)C(c1c(C)cc(C)cc1C)C2=O] | Mp: >250° C. |
| T6 | 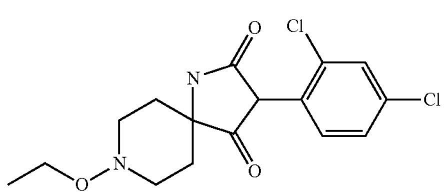 [SMILES: CCON1CCC2(CC1)NC(=O)C(c1ccc(Cl)cc1Cl)C2=O] | Mp: 244-245° C. |
| T7 | 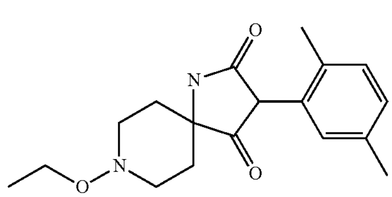 [SMILES: CCON1CCC2(CC1)NC(=O)C(c1cc(C)ccc1C)C2=O] | Mp: 166-167° C. |

TABLE T1-continued

| Compound Number | Structure | physical data |
|---|---|---|
| T8 | 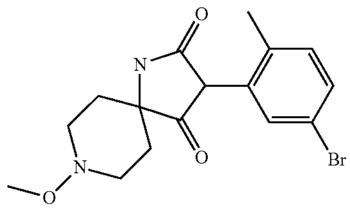 [SMILES: CON1CCC2(CC1)NC(=O)C(c1cc(Br)ccc1C)C2=O] | Mp: 194-196° C. |
| T9 | 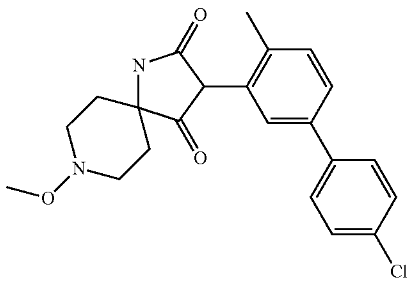 [SMILES: CON1CCC2(CC1)NC(=O)C(c1cc(-c3ccc(Cl)cc3)ccc1C)C2=O] | Solid, LC-MS: 399/401 (M + H)$^+$ |
| T10 | 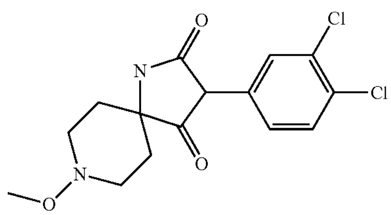 [SMILES: CON1CCC2(CC1)NC(=O)C(c1ccc(Cl)c(Cl)c1)C2=O] | Mp: 239-242° C. |
| T11 | 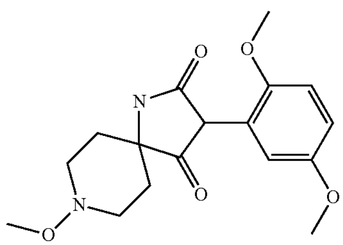 [SMILES: COc1ccc(OC)c(C2C(=O)NC3(CCN(OC)CC3)C2=O)c1] | Mp: 194-196° C. |
| T12 | 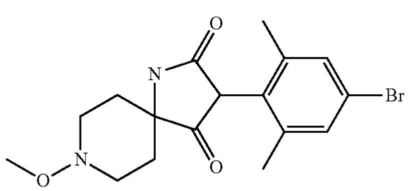 [SMILES: CON1CCC2(CC1)NC(=O)C(c1c(C)cc(Br)cc1C)C2=O] | Mp: 260-264° C. |
| T13 | 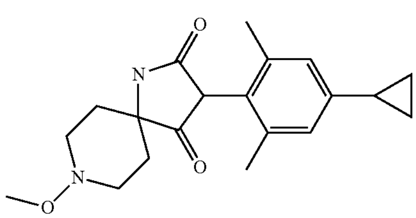 [SMILES: CON1CCC2(CC1)NC(=O)C(c1c(C)cc(C3CC3)cc1C)C2=O] | Mp: >250° C. |
| T14 | 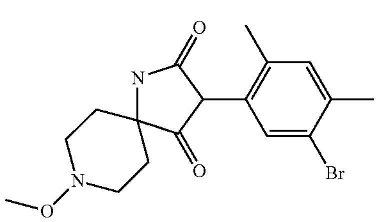 | Solid, LC-MS: 381/383 (M + H)$^+$ |

TABLE T1-continued

| Compound Number | Structure | physical data |
|---|---|---|
| T15 | 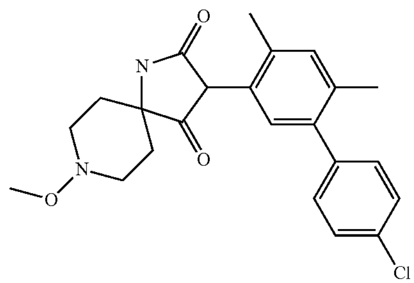 [SMILES: CON1CCC2(CC1)NC(=O)C(c1cc(-c3ccc(Cl)cc3)c(C)cc1C)C2=O] | Mp: 168-169° C. |
| T16 | 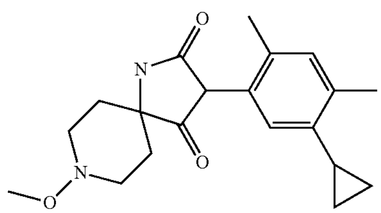 | Wax, LC-MS: 343 (M + H)+ |
| T17 | 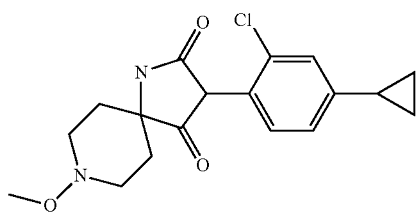 [SMILES: CON1CCC2(CC1)NC(=O)C(c1ccc(C3CC3)cc1Cl)C2=O] | Mp: 206-207° C. |
| T18 | 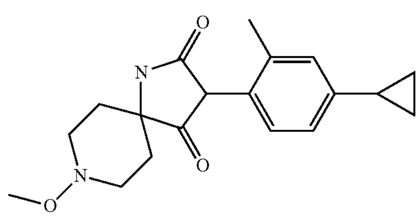 [SMILES: CON1CCC2(CC1)NC(=O)C(c1ccc(C3CC3)cc1C)C2=O] | Mp: 191-194° C. |
| T19 | 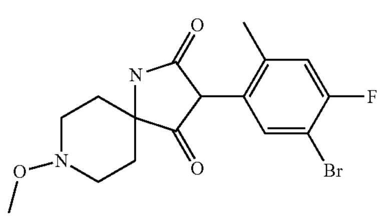 [SMILES: CON1CCC2(CC1)NC(=O)C(c1cc(Br)c(F)cc1C)C2=O] | Mp: 229-230° C. |
| T20 | 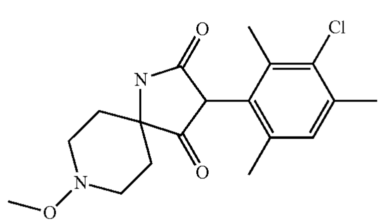 | Mp: >200° C. |

TABLE T1-continued

| Compound Number | Structure | physical data |
| --- | --- | --- |
| T21 | 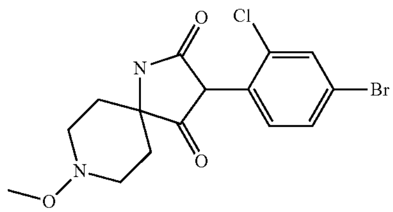 [SMILES: CON1CCC2(CC1)NC(=O)C(c1ccc(Br)cc1Cl)C2=O] | Mp: 167-169° C. |
| T22 | 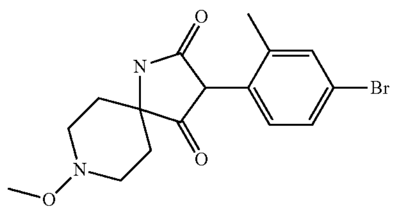 [SMILES: CON1CCC2(CC1)NC(=O)C(c1ccc(Br)cc1C)C2=O] | Mp: 187-189° C. |
| T23 | 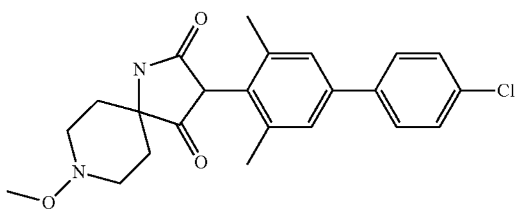 [SMILES: CON1CCC2(CC1)NC(=O)C(c1c(C)cc(-c3ccc(Cl)cc3)cc1C)C2=O] | Mp: 255-257° C. |

TABLE P1

| Compound Number | Structure | physical data |
| --- | --- | --- |
| P1 | 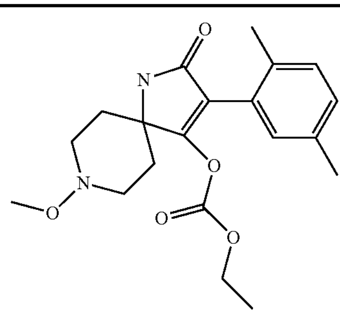 | Mp: 170-173° C. |
| P2 | 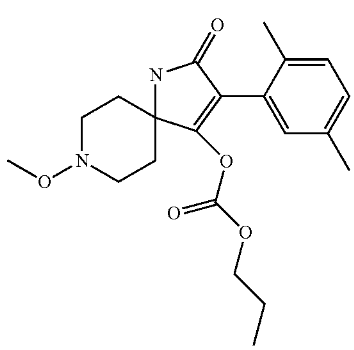 | Mp: 133-136° C. |

TABLE P1-continued

| Compound Number | Structure | physical data |
|---|---|---|
| P3 | 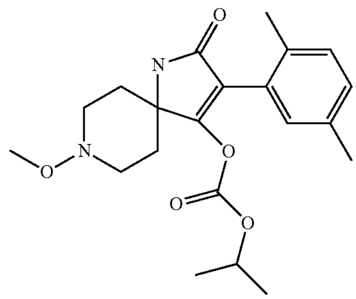 | Mp: 207-209° C. |
| P4 | 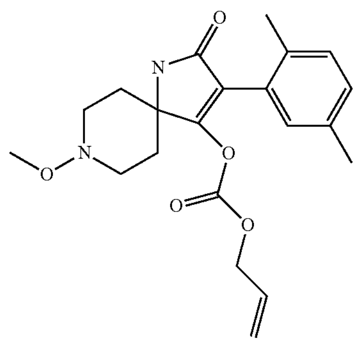 | Mp: 140-142° C. |
| P5 | 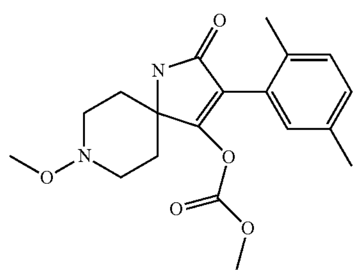 | Mp: 180° C. (decomposition) |
| P6 | 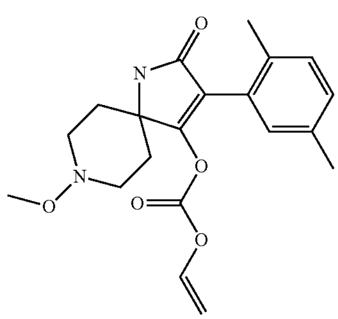 | Mp: 162-164° C. |
| P7 | 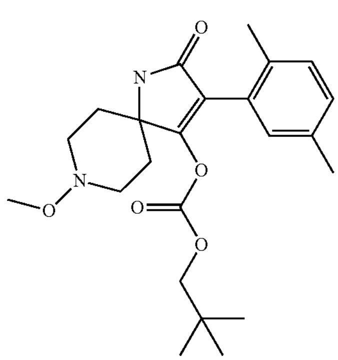 | Mp: 196-197° C. |

TABLE P1-continued

| Compound Number | Structure | physical data |
|---|---|---|
| P8 | 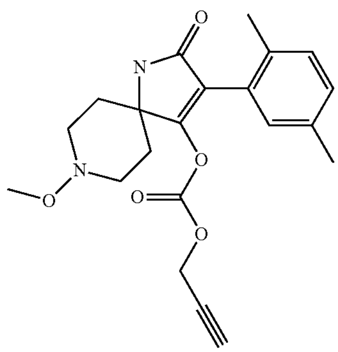 | Mp: 151-153° C. |
| P9 | 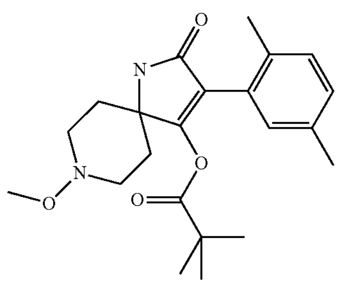 | Mp: 158-159° C. |
| P10 | 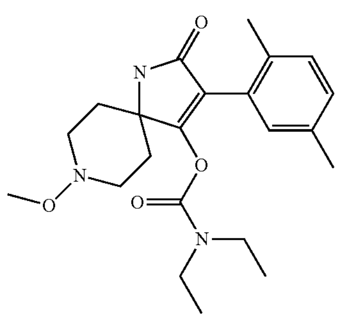 | Mp: 129-131° C. |
| P11 | 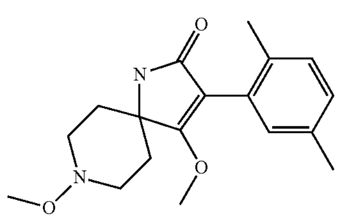 | Mp: 203-205° C. |
| P12 | 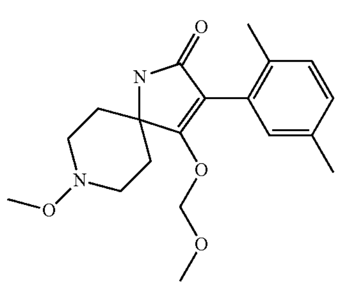 | Mp: 183-185° C. |

TABLE P1-continued

| Compound Number | Structure | physical data |
|---|---|---|
| P13 | 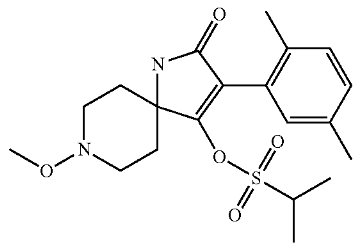 | Mp: 168-170° C. |
| P14 | 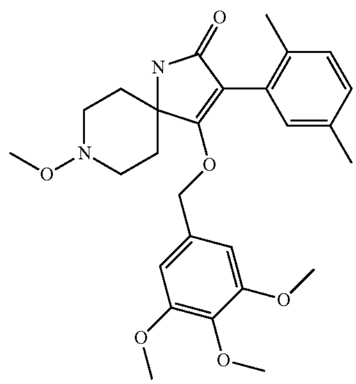 | Mp: 128-131° C. |
| P15 | 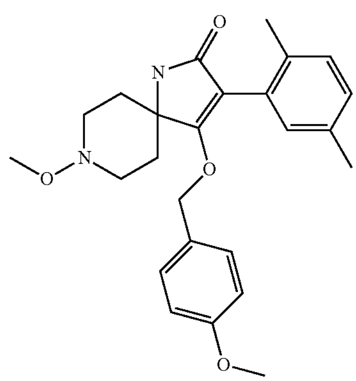 | Mp: 180-183° C. |
| P16 | 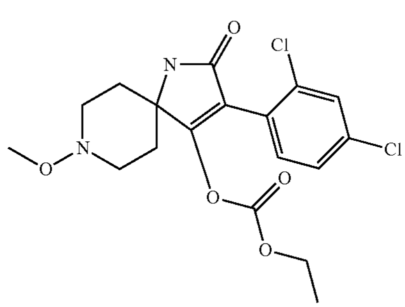 [SMILES: CCOC(=O)OC1=C(c2ccc(Cl)cc2Cl)C(=O)NC12CCN(OC)CC2] | Mp: 187-189° C. |

TABLE P1-continued

| Compound Number | Structure | physical data |
|---|---|---|
| P17 | 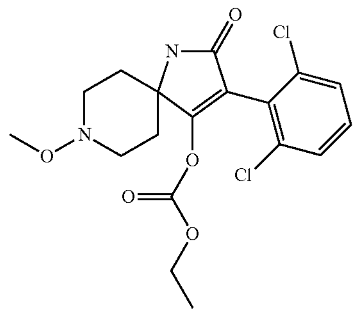 [SMILES: CCOC(=O)OC1=C(c2c(Cl)cccc2Cl)C(=O)NC12CCN(OC)CC2] | Mp: 229-232° C. |
| P18 | 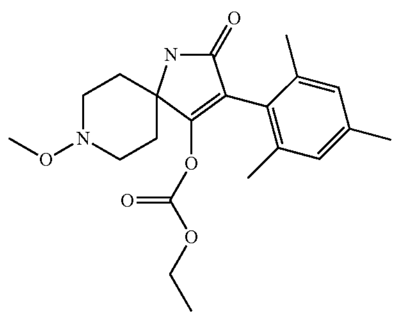 | Mp: 193-195° C. |
| P19 | 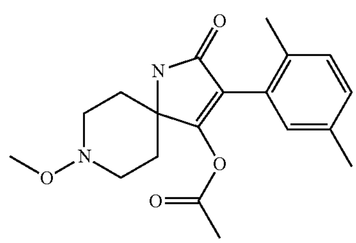 | Mp: 233-236° C. |
| P20 | 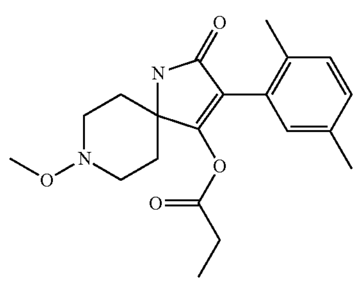 | Mp: 202-204° C. |
| P21 | 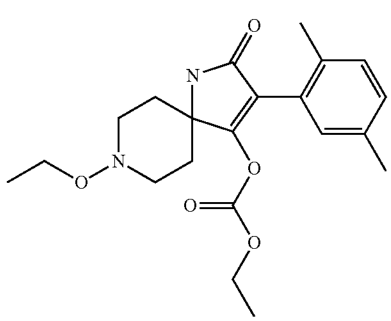 [SMILES: CCOC(=O)OC1=C(c2cc(C)ccc2C)C(=O)NC12CCN(OCC)CC2] | Mp: 167-168° C. |

TABLE P1-continued
| Compound Number | Structure | physical data |
|---|---|---|
| P22 | 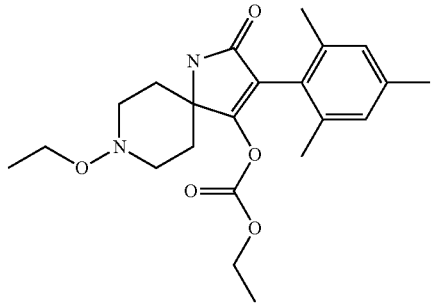 [SMILES: CCOC(=O)OC1=C(c2c(C)cc(C)cc2C)C(=O)NC12CCN(OCC)CC2] | Mp: 174-175° C. |
| P23 | 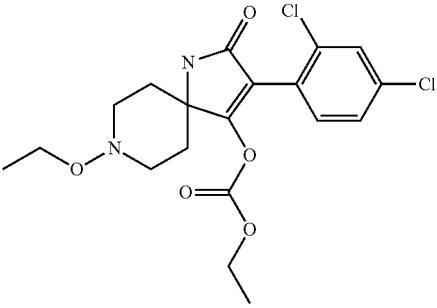 [SMILES: CCOC(=O)OC1=C(c2ccc(Cl)cc2Cl)C(=O)NC12CCN(OCC)CC2] | Mp: 183-184° C. |
| P24 | 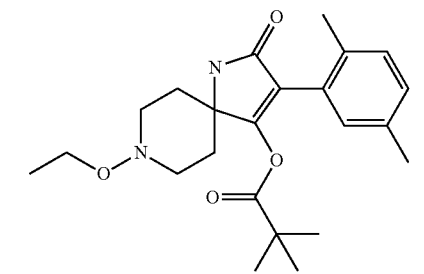 [SMILES: CCON1CCC2(CC1)NC(=O)C(c1cc(C)ccc1C)=C2OC(=O)C(C)(C)C] | Mp: 169-170° C. |
| P25 | 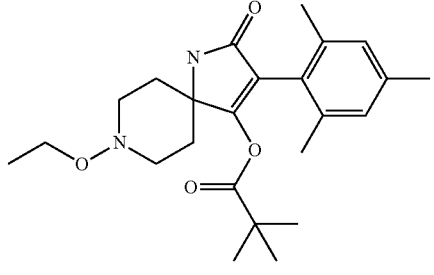 [SMILES: CCON1CCC2(CC1)NC(=O)C(c1c(C)cc(C)cc1C)=C2OC(=O)C(C)(C)C] | Mp: 230-231° C. |
| P26 | 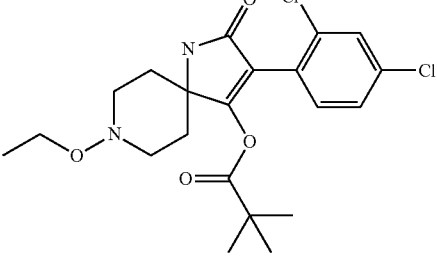 | Mp: 165-166° C. |

TABLE P1-continued
| Compound Number | Structure | physical data |
|---|---|---|
| P27 | 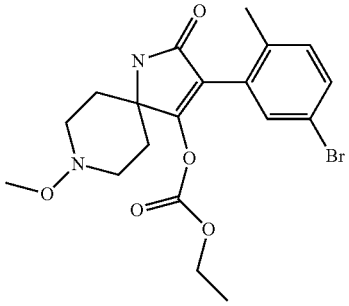 [SMILES: CCOC(=O)OC1=C(c2cc(Br)ccc2C)C(=O)NC12CCN(OC)CC2] | Mp: 205-209° C. |
| P28 | 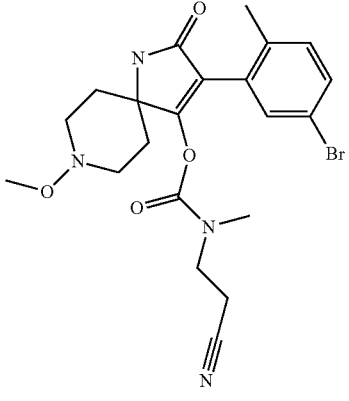 [SMILES: CON1CCC2(CC1)NC(=O)C(c1cc(Br)ccc1C)=C2OC(=O)N(C)CCC#N] | Mp: 197-200° C. |
| P29 | 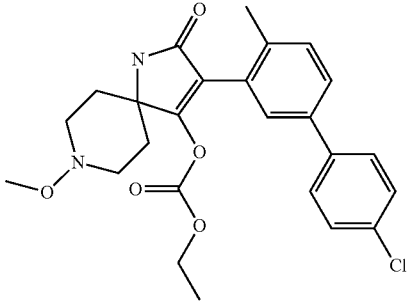 [SMILES: CCOC(=O)OC1=C(c2cc(-c3ccc(Cl)cc3)ccc2C)C(=O)NC12CCN(OC)CC2] | Mp: 209-211° C. |
| P30 | 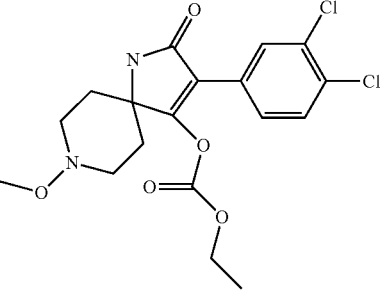 [SMILES: CCOC(=O)OC1=C(c2ccc(Cl)c(Cl)c2)C(=O)NC12CCN(OC)CC2] | Mp: 222-224° C. |

TABLE P1-continued

| Compound Number | Structure | physical data |
| --- | --- | --- |
| P31 | 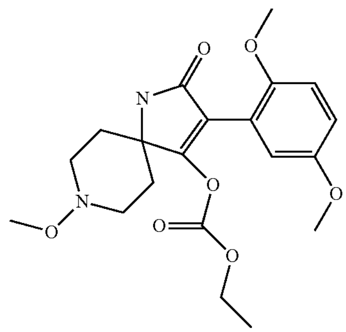 [SMILES: CCOC(=O)OC1=C(c2cc(OC)ccc2OC)C(=O)NC12CCN(OC)CC2] | Mp: 192-193° C. |
| P32 | 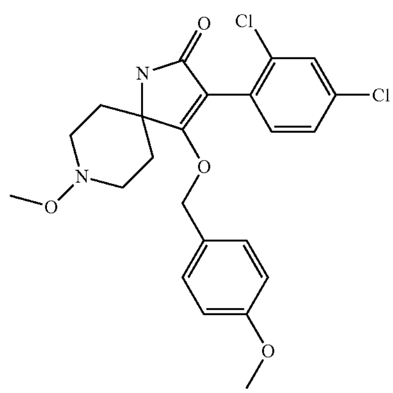 [SMILES: COc1ccc(COC2=C(c3ccc(Cl)cc3Cl)C(=O)NC23CCN(OC)CC3)cc1] | Mp: 111-113° C. |
| P33 | 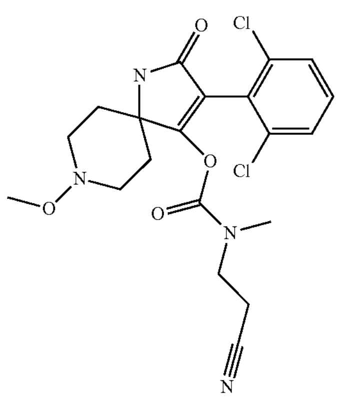 [SMILES: CON1CCC2(CC1)NC(=O)C(c1c(Cl)cccc1Cl)=C2OC(=O)N(C)CCC#N] | Mp: 239-242° C. |
| P34 | 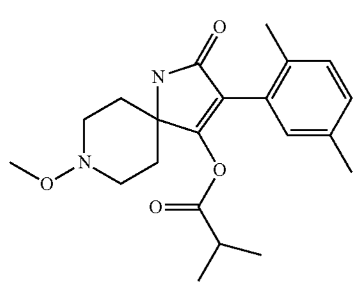 | Mp: 201-203° C. |

TABLE P1-continued
| Compound Number | Structure | physical data |
|---|---|---|
| P35 | 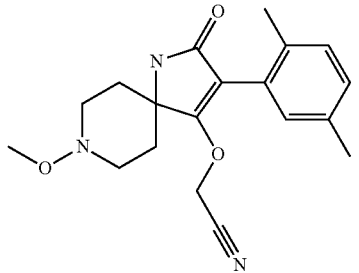 | Mp: 104-106° C. |
| P36 | 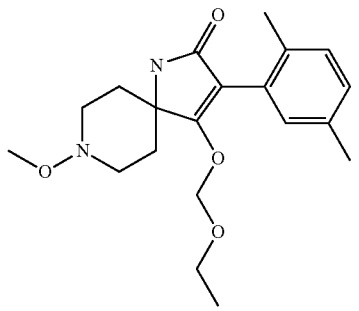 | Mp: 150-152° C. |
| P37 | 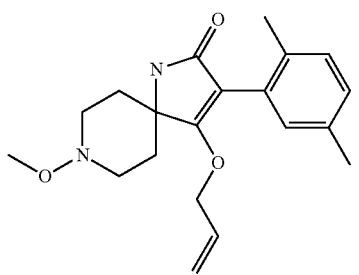 | Mp: 173-174° C. |
| P38 | 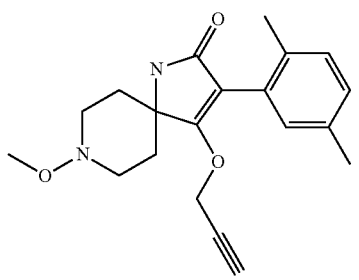 | Mp: 184-185° C. |
| P39 | 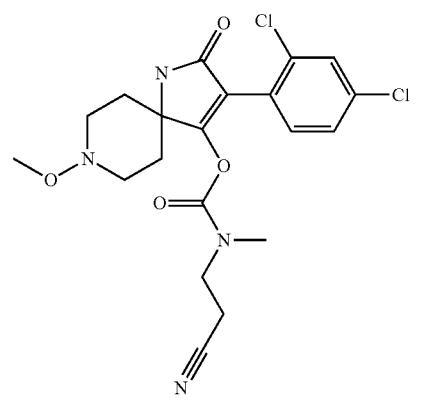 [SMILES: CON1CCC2(CC1)NC(=O)C(c1ccc(Cl)cc1Cl)=C2OC(=O)N(C)CCC#N] | Mp: 171-172° C. |

TABLE P1-continued
| Compound Number | Structure | physical data |
|---|---|---|
| P40 | 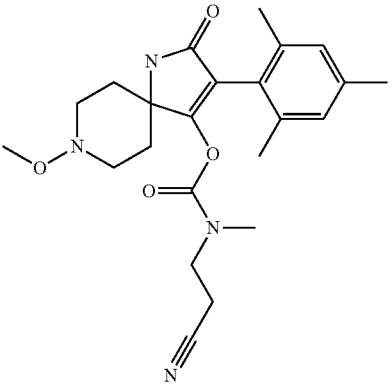 | Mp: 220-224° C. |
| P41 | 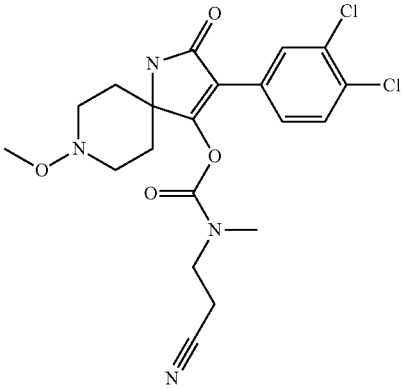 [SMILES: CON1CCC2(CC1)NC(=O)C(c1ccc(Cl)c(Cl)c1)=C2OC(=O)N(C)CCC#N] | Mp: 56-59° C. |
| P42 | 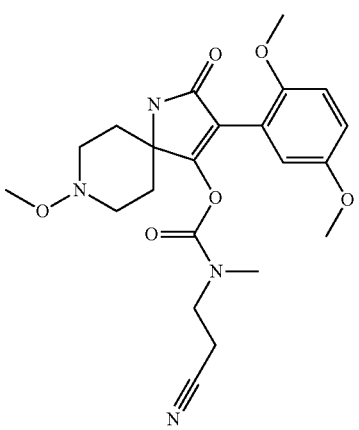 [SMILES: COc1ccc(OC)c(C2=C(OC(=O)N(C)CCC#N)C3(CCN(OC)CC3)NC2=O)c1] | Mp: 187-189° C. |
| P43 | 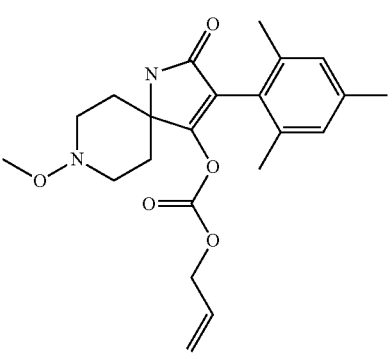 | Mp: 174-176° C. |

TABLE P1-continued
| Compound Number | Structure | physical data |
|---|---|---|
| P44 | 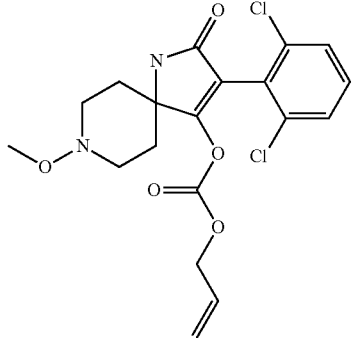 [SMILES: C=CCOC(=O)OC1=C(c2c(Cl)cccc2Cl)C(=O)NC12CCN(OC)CC2] | Mp: 203-205° C. |
| P45 | 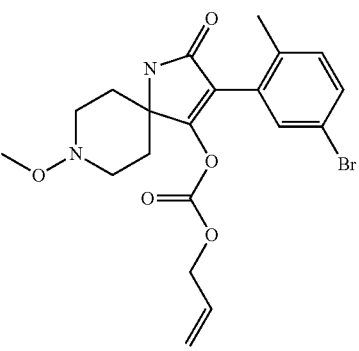 [SMILES: C=CCOC(=O)OC1=C(c2cc(Br)ccc2C)C(=O)NC12CCN(OC)CC2] | Mp: 157-158° C. |
| P46 | 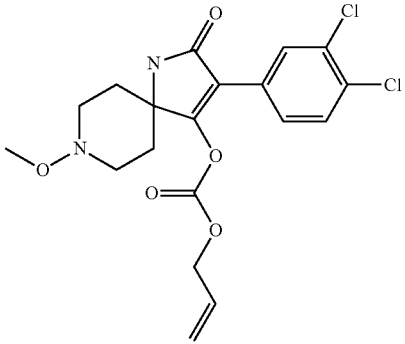 [SMILES: C=CCOC(=O)OC1=C(c2ccc(Cl)c(Cl)c2)C(=O)NC12CCN(OC)CC2] | Mp: 210-213° C. |
| P47 | 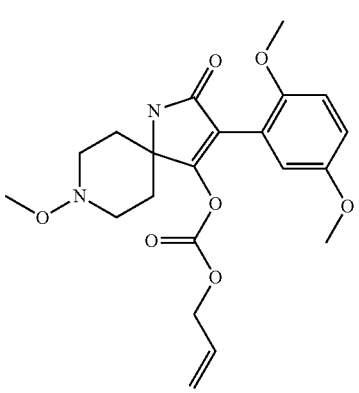 [SMILES: C=CCOC(=O)OC1=C(c2cc(OC)ccc2OC)C(=O)NC12CCN(OC)CC2] | Mp: 156-157° C. |

TABLE P1-continued

| Compound Number | Structure | physical data |
|---|---|---|
| P48 | 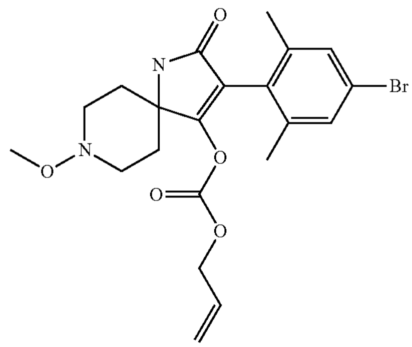 [SMILES: C=CCOC(=O)OC1=C(c2c(C)cc(Br)cc2C)C(=O)NC12CCN(OC)CC2] | Mp: 207-211° C. |
| P49 | 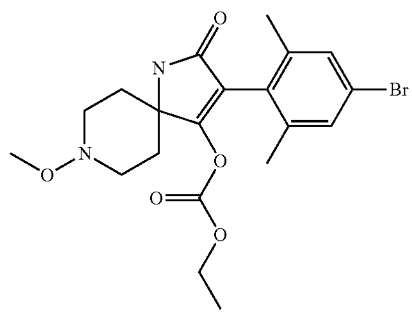 [SMILES: CCOC(=O)OC1=C(c2c(C)cc(Br)cc2C)C(=O)NC12CCN(OC)CC2] | Mp: 185-187° C. |
| P50 | 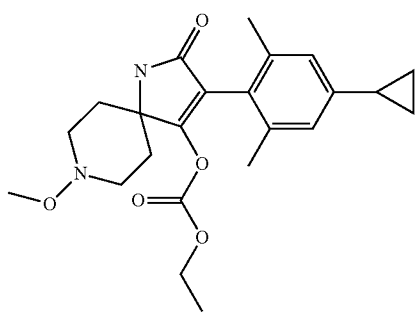 [SMILES: CCOC(=O)OC1=C(c2c(C)cc(C3CC3)cc2C)C(=O)NC12CCN(OC)CC2] | Mp: 215-216° C. |
| P51 | 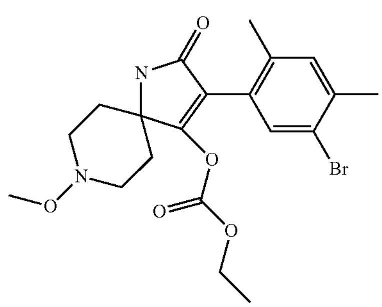 | Mp: 206-209° C. |
| P52 | 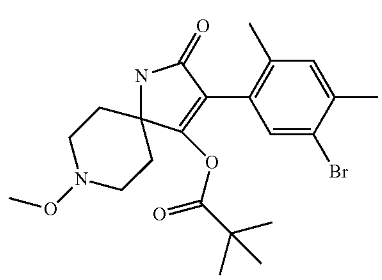 | Mp: 225-226° C. |

TABLE P1-continued

| Compound Number | Structure | physical data |
|---|---|---|
| P53 | 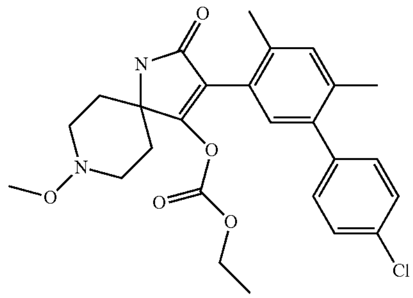 [SMILES: CCOC(=O)OC1=C(c2cc(-c3ccc(Cl)cc3)c(C)cc2C)C(=O)NC12CCN(OC)CC2] | Mp: 211-213° C. |
| P54 | 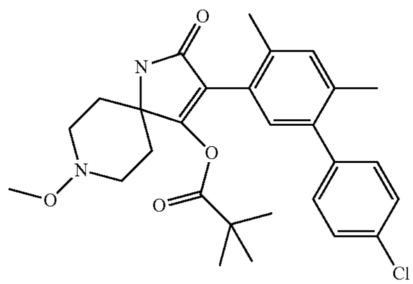 [SMILES: CON1CCC2(CC1)NC(=O)C(c1cc(-c3ccc(Cl)cc3)c(C)cc1C)=C2OC(=O)C(C)(C)C] | Mp: 229-230° C. |
| P55 | 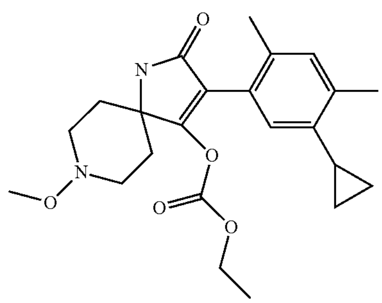 | Mp: 174-176° C. |
| P56 | 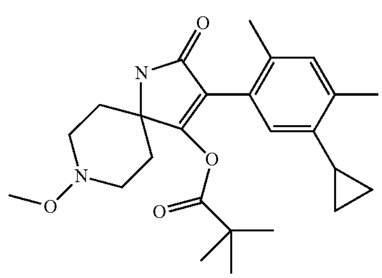 | Mp: 218-219° C. |
| P57 | 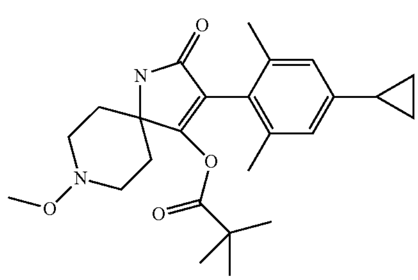 [SMILES: CON1CCC2(CC1)NC(=O)C(c1c(C)cc(C3CC3)cc1C)=C2OC(=O)C(C)(C)C] | Mp: >200° C. |

TABLE P1-continued

| Compound Number | Structure | physical data |
|---|---|---|
| P58 | 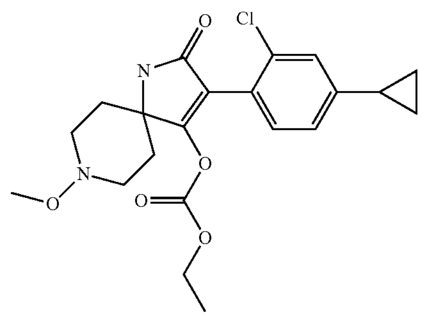 [SMILES: CCOC(=O)OC1=C(c2ccc(C3CC3)cc2Cl)C(=O)NC12CCN(OC)CC2] | Mp: 190-192° C. |
| P59 | 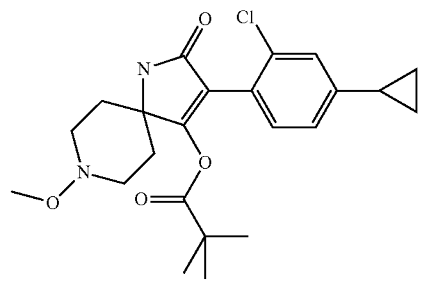 [SMILES: CON1CCC2(CC1)NC(=O)C(c1ccc(C3CC3)cc1Cl)=C2OC(=O)C(C)(C)C] | Mp: 195-197° C. |
| P60 | 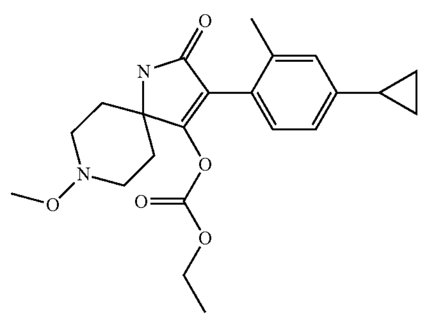 [SMILES: CCOC(=O)OC1=C(c2ccc(C3CC3)cc2C)C(=O)NC12CCN(OC)CC2] | Mp: 193-195° C. |
| P61 | 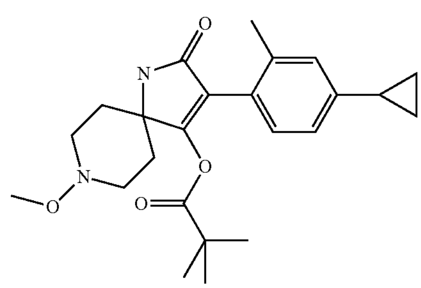 [SMILES: CON1CCC2(CC1)NC(=O)C(c1ccc(C3CC3)cc1C)=C2OC(=O)C(C)(C)C] | Mp: 244-245° C. |
| P62 | 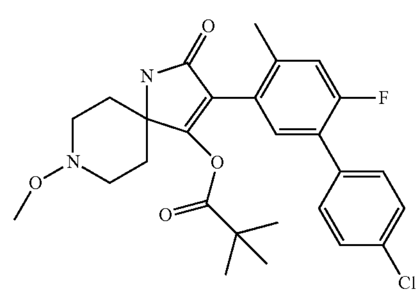 [SMILES: CON1CCC2(CC1)NC(=O)C(c1cc(-c3ccc(Cl)cc3)c(F)cc1C)=C2OC(=O)C(C)(C)C] | Mp: 150-151° C. |

TABLE P1-continued

| Compound Number | Structure | physical data |
|---|---|---|
| P63 | 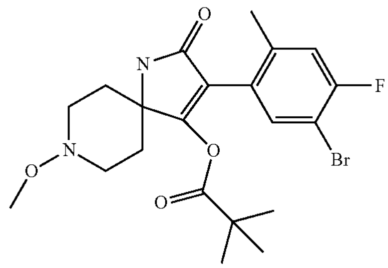 [SMILES: CON1CCC2(CC1)NC(=O)C(c1cc(Br)c(F)cc1C)=C2OC(=O)C(C)(C)C] | Mp: 216-217° C. |
| P64 | 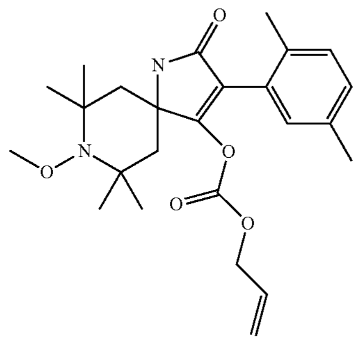 | Solid, LC-MS: 443 (M + H)+ |
| P65 | 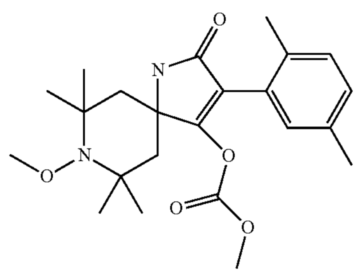 | Solid, LC-MS: 417 (M + H)+ |
| P66 | 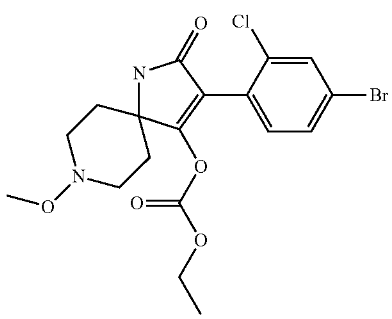 [SMILES: CCOC(=O)OC1=C(c2ccc(Br)cc2Cl)C(=O)NC12CCN(OC)CC2] | Mp: 199-201° C. |
| P67 | 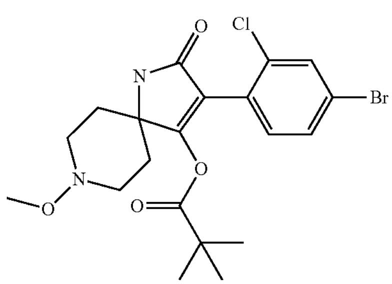 [SMILES: CON1CCC2(CC1)NC(=O)C(c1ccc(Br)cc1Cl)=C2OC(=O)C(C)(C)C] | Mp: 223-225° C. |

TABLE P1-continued
| Compound Number | Structure | physical data |
|---|---|---|
| P68 | 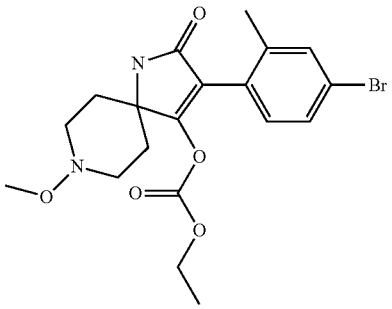 [SMILES: CCOC(=O)OC1=C(c2ccc(Br)cc2C)C(=O)NC12CCN(OC)CC2] | Mp: 201-203° C. |
| P69 | 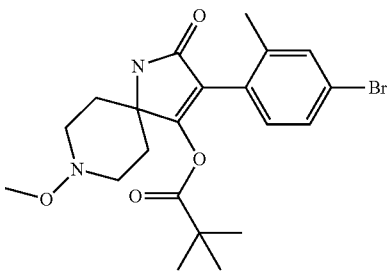 [SMILES: CON1CCC2(CC1)NC(=O)C(c1ccc(Br)cc1C)=C2OC(=O)C(C)(C)C] | Mp: 239-240° C. |
| P70 | 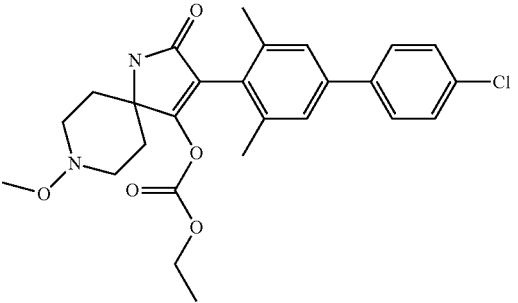 [SMILES: CCOC(=O)OC1=C(c2c(C)cc(-c3ccc(Cl)cc3)cc2C)C(=O)NC12CCN(OC)CC2] | Mp: 217-219° C. |
| P71 | 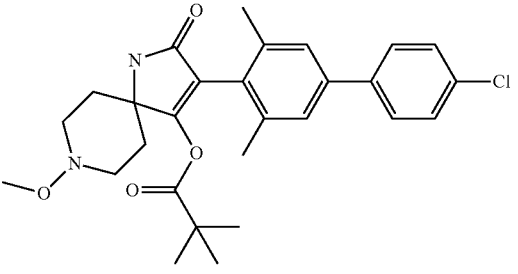 [SMILES: CON1CCC2(CC1)NC(=O)C(c1c(C)cc(-c3ccc(Cl)cc3)cc1C)=C2OC(=O)C(C)(C)C] | Mp: >250° C. |
| P72 | 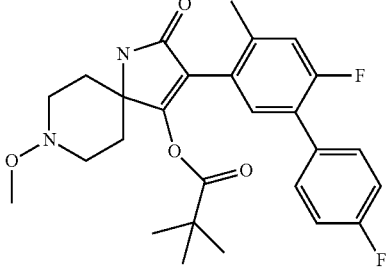 [SMILES: CON1CCC2(CC1)NC(=O)C(c1cc(-c3ccc(F)cc3)c(F)cc1C)=C2OC(=O)C(C)(C)C] | Mp: 101-104° C. |

TABLE P1-continued

| Compound Number | Structure | physical data |
|---|---|---|
| P73 | (structure shown) | Mp: 161-164° C. |

Tables 1 to 22 below illustrate the compounds used according to the invention.

Table 1: This table discloses the 262 compounds of the formula I:

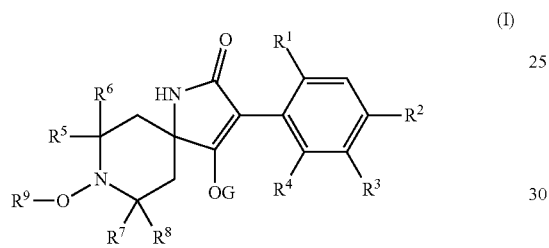

(I)

wherein $R^9$ is $CH_3$, $R^5$, $R^6$, $R^7$ and $R^8$ are hydrogen, G is hydrogen and $R^1$, $R^2$, $R^3$ and $R^4$ are as defined below:

| Compound Number | $R^1$ | $R^2$ | $R^3$ | $R^4$ |
|---|---|---|---|---|
| 1.001 | $CH_3$ | H | H | H |
| 1.002 | $CH_3$ | $CH_3$ | H | H |
| 1.003 | $CH_3$ | H | $CH_3$ | H |
| 1.004 | $CH_3$ | H | H | $CH_3$ |
| 1.005 | $CH_3$ | $CH_3$ | $CH_3$ | H |
| 1.006 | $CH_3$ | $CH_3$ | H | $CH_3$ |
| 1.007 | $CH_3$ | $CH_3$ | $CH_3$ | $CH_3$ |
| 1.008 | $CH_3$ | Cl | H | H |
| 1.009 | $CH_3$ | Cl | H | $CH_3$ |
| 1.010 | $CH_3$ | Cl | H | $OCH_3$ |
| 1.011 | $CH_3$ | H | Cl | H |
| 1.012 | $CH_3$ | H | H | Cl |
| 1.013 | $CH_3$ | $CH_3$ | Cl | H |
| 1.014 | $CH_3$ | $CH_3$ | H | Cl |
| 1.015 | $CH_3$ | H | Cl | $CH_3$ |
| 1.016 | $CH_3$ | $CH_3$ | Cl | $CH_3$ |
| 1.017 | $CH_3$ | Br | H | H |
| 1.018 | $CH_3$ | Br | H | $CH_3$ |
| 1.019 | $CH_3$ | Br | H | $OCH_3$ |
| 1.020 | $CH_3$ | H | Br | H |
| 1.021 | $CH_3$ | H | H | Br |
| 1.022 | $CH_3$ | $CH_3$ | Br | H |
| 1.023 | $CH_3$ | $CH_3$ | H | Br |
| 1.024 | $CH_3$ | H | Br | $CH_3$ |
| 1.025 | $CH_3$ | $CH_3$ | Br | $CH_3$ |
| 1.026 | $CH_3$ | $CH_3O$ | H | H |
| 1.027 | $CH_3$ | $CH_3O$ | H | $CH_3$ |
| 1.028 | $CH_3$ | $CH_3O$ | H | Cl |
| 1.029 | $CH_3$ | $CH_3O$ | H | Br |
| 1.030 | $CH_3$ | $CH_3CH_2O$ | H | H |
| 1.031 | $CH_3$ | $CH_3CH_2O$ | H | $CH_3$ |
| 1.032 | $CH_3$ | $CH_3CH_2O$ | H | Cl |

-continued

| Compound Number | $R^1$ | $R^2$ | $R^3$ | $R^4$ |
|---|---|---|---|---|
| 1.033 | $CH_3$ | $CH_3CH_2O$ | H | Br |
| 1.034 | $CH_3$ | H | $CH_3O$ | H |
| 1.035 | $CH_3$ | H | H | $CH_3O$ |
| 1.036 | $CH_3$ | $CH_3$ | $CH_3O$ | H |
| 1.037 | $CH_3$ | $CH_3$ | H | $CH_3O$ |
| 1.038 | $CH_3$ | H | $CH_3O$ | $CH_3$ |
| 1.039 | $CH_3$ | $CH_3$ | $CH_3O$ | $CH_3$ |
| 1.040 | $CH_3$ | —CH=$CH_2$ | H | $CH_3$ |
| 1.041 | $CH_3$ | $CH_3$ | H | —CH=$CH_2$ |
| 1.042 | $CH_3$ | —C•CH | H | $CH_3$ |
| 1.043 | $CH_3$ | $CH_3$ | H | —C•CH |
| 1.044 | $CH_3$ | —CH=$CH_2$ | H | —CH=$CH_2$ |
| 1.045 | $CH_3$ | $CH_2CH_3$ | H | $CH_3$ |
| 1.046 | $CH_3$ | phenyl | H | $CH_3$ |
| 1.047 | $CH_3$ | 2-fluorophenyl | H | $CH_3$ |
| 1.048 | $CH_3$ | 2-chlorophenyl | H | $CH_3$ |
| 1.049 | $CH_3$ | 2-trifluoromethylphenyl | H | $CH_3$ |
| 1.050 | $CH_3$ | 2-nitrophenyl | H | $CH_3$ |
| 1.051 | $CH_3$ | 2-methylphenyl | H | $CH_3$ |
| 1.052 | $CH_3$ | 2-methanesulfonylphenyl | H | $CH_3$ |
| 1.053 | $CH_3$ | 2-cyanophenyl | H | $CH_3$ |
| 1.054 | $CH_3$ | 3-fluorophenyl | H | $CH_3$ |
| 1.055 | $CH_3$ | 3-chlorophenyl | H | $CH_3$ |
| 1.056 | $CH_3$ | 3-trifluoromethylphenyl | H | $CH_3$ |
| 1.057 | $CH_3$ | 3-nitrophenyl | H | $CH_3$ |
| 1.058 | $CH_3$ | 3-methylphenyl | H | $CH_3$ |
| 1.059 | $CH_3$ | 3-methanesulfonylphenyl | H | $CH_3$ |
| 1.060 | $CH_3$ | 3-cyanophenyl | H | $CH_3$ |
| 1.061 | $CH_3$ | 4-fluorophenyl | H | $CH_3$ |
| 1.062 | $CH_3$ | 4-chlorophenyl | H | $CH_3$ |
| 1.063 | $CH_3$ | 4-bromophenyl | H | $CH_3$ |
| 1.064 | $CH_3$ | 4-difluoromethoxyphenyl | H | $CH_3$ |
| 1.065 | $CH_3$ | 2-fluoro-4-chlorophenyl | H | $CH_3$ |
| 1.066 | $CH_3$ | 2-chloro-4-chlorophenyl | H | $CH_3$ |
| 1.067 | $CH_3$ | 2-methyl-4-chlorophenyl | H | $CH_3$ |
| 1.068 | $CH_3$ | 4-trifluoromethylphenyl | H | $CH_3$ |
| 1.069 | $CH_3$ | 4-nitrophenyl | H | $CH_3$ |
| 1.070 | $CH_3$ | 4-methylphenyl | H | $CH_3$ |
| 1.071 | $CH_3$ | 4-methanesulfonylphenyl | H | $CH_3$ |
| 1.072 | $CH_3$ | 4-cyanophenyl | H | $CH_3$ |
| 1.073 | $CH_3$ | H | phenyl | H |
| 1.074 | $CH_3$ | H | 2-fluorophenyl | H |
| 1.075 | $CH_3$ | H | 2-chlorophenyl | H |
| 1.076 | $CH_3$ | H | 2-trifluoromethylphenyl | H |
| 1.077 | $CH_3$ | H | 2-nitrophenyl | H |
| 1.078 | $CH_3$ | H | 2-methylphenyl | H |
| 1.079 | $CH_3$ | H | 2-methylsulfonylphenyl | H |
| 1.080 | $CH_3$ | H | 2-cyanophenyl | H |
| 1.081 | $CH_3$ | H | 3-fluorophenyl | H |
| 1.082 | $CH_3$ | H | 3-chlorophenyl | H |
| 1.083 | $CH_3$ | H | 3-trifluoromethylphenyl | H |
| 1.084 | $CH_3$ | H | 3-nitrophenyl | H |
| 1.085 | $CH_3$ | H | 3-methylphenyl | H |
| 1.086 | $CH_3$ | H | 3-methylsulfonylphenyl | H |
| 1.087 | $CH_3$ | H | 3-cyanophenyl | H |
| 1.088 | $CH_3$ | H | 4-fluorophenyl | H |
| 1.089 | $CH_3$ | H | 4-chlorophenyl | H |
| 1.090 | $CH_3$ | H | 4-bromophenyl | H |
| 1.091 | $CH_3$ | H | 4-difluoromethoxyphenyl | H |
| 1.092 | $CH_3$ | H | 2-fluoro-4-chlorophenyl | H |
| 1.093 | $CH_3$ | H | 2-chloro-4-chlorophenyl | H |
| 1.094 | $CH_3$ | H | 2-methyl-4-chlorophenyl | H |
| 1.095 | $CH_3$ | H | 4-trifluoromethylphenyl | H |
| 1.096 | $CH_3$ | H | 4-nitrophenyl | H |
| 1.097 | $CH_3$ | H | 4-methylphenyl | H |
| 1.098 | $CH_3$ | H | 4-methylsulfonylphenyl | H |
| 1.099 | $CH_3$ | H | 4-cyanophenyl | H |
| 1.100 | $CH_2CH_3$ | H | H | H |
| 1.101 | $CH_2CH_3$ | $CH_3$ | H | H |
| 1.102 | $CH_2CH_3$ | H | $CH_3$ | H |
| 1.103 | $CH_2CH_3$ | H | H | $CH_3$ |
| 1.104 | $CH_2CH_3$ | $CH_3$ | $CH_3$ | H |
| 1.105 | $CH_2CH_3$ | $CH_3$ | H | $CH_3$ |
| 1.106 | $CH_2CH_3$ | $CH_3$ | $CH_3$ | $CH_3$ |
| 1.107 | $CH_2CH_3$ | Cl | H | H |
| 1.108 | $CH_2CH_3$ | Cl | H | $CH_3$ |
| 1.109 | $CH_2CH_3$ | Cl | H | $OCH_3$ |

-continued

| Compound Number | $R^1$ | $R^2$ | $R^3$ | $R^4$ |
|---|---|---|---|---|
| 1.110 | $CH_2CH_3$ | H | Cl | H |
| 1.111 | $CH_2CH_3$ | H | H | Cl |
| 1.112 | $CH_2CH_3$ | $CH_3$ | Cl | H |
| 1.113 | $CH_2CH_3$ | $CH_3$ | H | Cl |
| 1.114 | $CH_2CH_3$ | H | Cl | $CH_3$ |
| 1.115 | $CH_2CH_3$ | $CH_3$ | Cl | $CH_3$ |
| 1.116 | $CH_2CH_3$ | Br | H | H |
| 1.117 | $CH_2CH_3$ | Br | H | $CH_3$ |
| 1.118 | $CH_2CH_3$ | Br | H | $OCH_3$ |
| 1.119 | $CH_2CH_3$ | H | Br | H |
| 1.120 | $CH_2CH_3$ | H | H | Br |
| 1.121 | $CH_2CH_3$ | $CH_3$ | Br | H |
| 1.122 | $CH_2CH_3$ | $CH_3$ | H | Br |
| 1.123 | $CH_2CH_3$ | H | Br | $CH_3$ |
| 1.124 | $CH_2CH_3$ | $CH_3$ | Br | $CH_3$ |
| 1.125 | $CH_2CH_3$ | $CH_3O$ | H | H |
| 1.126 | $CH_2CH_3$ | $CH_3O$ | H | $CH_3$ |
| 1.127 | $CH_2CH_3$ | $CH_3O$ | H | Cl |
| 1.128 | $CH_2CH_3$ | $CH_3O$ | H | Br |
| 1.129 | $CH_2CH_3$ | $CH_3CH_2O$ | H | H |
| 1.130 | $CH_2CH_3$ | $CH_3CH_2O$ | H | $CH_3$ |
| 1.131 | $CH_2CH_3$ | $CH_3CH_2O$ | H | Cl |
| 1.132 | $CH_2CH_3$ | $CH_3CH_2O$ | H | Br |
| 1.133 | $CH_2CH_3$ | H | $CH_3O$ | H |
| 1.134 | $CH_2CH_3$ | H | H | $CH_3O$ |
| 1.135 | $CH_2CH_3$ | $CH_3$ | $CH_3O$ | H |
| 1.136 | $CH_2CH_3$ | $CH_3$ | H | $CH_3O$ |
| 1.137 | $CH_2CH_3$ | H | $CH_3O$ | $CH_3$ |
| 1.138 | $CH_2CH_3$ | $CH_3$ | $CH_3O$ | $CH_3$ |
| 1.139 | $CH_2CH_3$ | —CH=$CH_2$ | H | $CH_3$ |
| 1.140 | $CH_2CH_3$ | $CH_3$ | H | —CH=$CH_2$ |
| 1.141 | $CH_2CH_3$ | —C•CH | H | $CH_3$ |
| 1.142 | $CH_2CH_3$ | $CH_3$ | H | —C•CH |
| 1.143 | $CH_2CH_3$ | —CH=$CH_2$ | H | —CH=$CH_2$ |
| 1.144 | $CH_2CH_3$ | $CH_2CH_3$ | H | $CH_3$ |
| 1.145 | $CH_2CH_3$ | phenyl | H | $CH_3$ |
| 1.146 | $CH_2CH_3$ | 2-fluorophenyl | H | $CH_3$ |
| 1.147 | $CH_2CH_3$ | 2-chlorophenyl | H | $CH_3$ |
| 1.148 | $CH_2CH_3$ | 2-trifluoromethylphenyl | H | $CH_3$ |
| 1.149 | $CH_2CH_3$ | 2-nitrophenyl | H | $CH_3$ |
| 1.150 | $CH_2CH_3$ | 2-methylphenyl | H | $CH_3$ |
| 1.151 | $CH_2CH_3$ | 2-methylsulfonylphenyl | H | $CH_3$ |
| 1.152 | $CH_2CH_3$ | 2-cyanophenyl | H | $CH_3$ |
| 1.153 | $CH_2CH_3$ | 3-fluorophenyl | H | $CH_3$ |
| 1.154 | $CH_2CH_3$ | 3-chlorophenyl | H | $CH_3$ |
| 1.155 | $CH_2CH_3$ | 3-trifluoromethylphenyl | H | $CH_3$ |
| 1.156 | $CH_2CH_3$ | 3-nitrophenyl | H | $CH_3$ |
| 1.157 | $CH_2CH_3$ | 3-methylphenyl | H | $CH_3$ |
| 1.158 | $CH_2CH_3$ | 3-methylsulfonylphenyl | H | $CH_3$ |
| 1.159 | $CH_2CH_3$ | 3-cyanophenyl | H | $CH_3$ |
| 1.160 | $CH_2CH_3$ | 4-fluorophenyl | H | $CH_3$ |
| 1.161 | $CH_2CH_3$ | 4-chlorophenyl | H | $CH_3$ |
| 1.162 | $CH_2CH_3$ | 4-bromophenyl | H | $CH_3$ |
| 1.163 | $CH_2CH_3$ | 4-difluoromethoxyphenyl | H | $CH_3$ |
| 1.164 | $CH_2CH_3$ | 2-fluoro-4-chlorophenyl | H | $CH_3$ |
| 1.165 | $CH_2CH_3$ | 2-chloro-4-chlorophenyl | H | $CH_3$ |
| 1.166 | $CH_2CH_3$ | 2-methyl-4-chlorophenyl | H | $CH_3$ |
| 1.167 | $CH_2CH_3$ | 4-trifluoromethylphenyl | H | $CH_3$ |
| 1.168 | $CH_2CH_3$ | 4-nitrophenyl | H | $CH_3$ |
| 1.169 | $CH_2CH_3$ | 4-methylphenyl | H | $CH_3$ |
| 1.170 | $CH_2CH_3$ | 4-methylsulfonylphenyl | H | $CH_3$ |
| 1.171 | $CH_2CH_3$ | 4-cyanophenyl | H | $CH_3$ |
| 1.172 | $CH_2CH_3$ | H | phenyl | H |
| 1.173 | $CH_2CH_3$ | H | 2-fluorophenyl | H |
| 1.174 | $CH_2CH_3$ | H | 2-chlorophenyl | H |
| 1.175 | $CH_2CH_3$ | H | 2-trifluoromethylphenyl | H |
| 1.176 | $CH_2CH_3$ | H | 2-nitrophenyl | H |
| 1.177 | $CH_2CH_3$ | H | 2-methylphenyl | H |
| 1.178 | $CH_2CH_3$ | H | 2-methylsulfonylphenyl | H |
| 1.179 | $CH_2CH_3$ | H | 2-cyanophenyl | H |
| 1.180 | $CH_2CH_3$ | H | 3-fluorophenyl | H |
| 1.181 | $CH_2CH_3$ | H | 3-chlorophenyl | H |
| 1.182 | $CH_2CH_3$ | H | 3-trifluoromethylphenyl | H |
| 1.183 | $CH_2CH_3$ | H | 3-nitrophenyl | H |
| 1.184 | $CH_2CH_3$ | H | 3-methylphenyl | H |
| 1.185 | $CH_2CH_3$ | H | 3-methylsulfonylphenyl | H |
| 1.186 | $CH_2CH_3$ | H | 3-cyanophenyl | H |

-continued

| Compound Number | $R^1$ | $R^2$ | $R^3$ | $R^4$ |
|---|---|---|---|---|
| 1.187 | $CH_2CH_3$ | H | 4-fluorophenyl | H |
| 1.188 | $CH_2CH_3$ | H | 4-chlorophenyl | H |
| 1.189 | $CH_2CH_3$ | H | 4-bromophenyl | H |
| 1.190 | $CH_2CH_3$ | H | 4-difluoromethoxyphenyl | H |
| 1.191 | $CH_2CH_3$ | H | 2-fluoro-4-chlorophenyl | H |
| 1.192 | $CH_2CH_3$ | H | 2-chloro-4-chlorophenyl | H |
| 1.193 | $CH_2CH_3$ | H | 2-methyl-4-chlorophenyl | H |
| 1.194 | $CH_2CH_3$ | H | 4-trifluoromethylphenyl | H |
| 1.195 | $CH_2CH_3$ | H | 4-nitrophenyl | H |
| 1.196 | $CH_2CH_3$ | H | 4-methylphenyl | H |
| 1.197 | $CH_2CH_3$ | H | 4-methylsulfonylphenyl | H |
| 1.198 | $CH_2CH_3$ | H | 4-cyanophenyl | H |
| 1.199 | $CH_2CH_3$ | $CH_3$ | H | $CH_2CH_3$ |
| 1.200 | $CH_2CH_3$ | $CH_2CH_3$ | H | $CH_2CH_3$ |
| 1.201 | $CH_2CH_3$ | Cl | H | $CH_2CH_3$ |
| 1.202 | $CH_2CH_3$ | Br | H | $CH_2CH_3$ |
| 1.203 | $CH_2CH_3$ | $NO_2$ | H | $CH_2CH_3$ |
| 1.204 | $CH_2CH_3$ | $CH_3O$ | H | $CH_2CH_3$ |
| 1.205 | $CH_2CH_3$ | $CH_3S$ | H | $CH_2CH_3$ |
| 1.206 | $CH_2CH_3$ | $CH_3SO_2$ | H | $CH_2CH_3$ |
| 1.207 | $CH_2CH_3$ | $CH_2=CH$ | H | $CH_2CH_3$ |
| 1.208 | $CH_2CH_3$ | —C•CH | H | $CH_2CH_3$ |
| 1.209 | $CH_2CH_3$ | phenyl | H | $CH_2CH_3$ |
| 1.210 | $CH_2CH_3$ | 2-fluorophenyl | H | $CH_2CH_3$ |
| 1.211 | $CH_2CH_3$ | 2-chlorophenyl | H | $CH_2CH_3$ |
| 1.212 | $CH_2CH_3$ | 2-trifluoromethylphenyl | H | $CH_2CH_3$ |
| 1.213 | $CH_2CH_3$ | 2-nitrophenyl | H | $CH_2CH_3$ |
| 1.214 | $CH_2CH_3$ | 2-methylphenyl | H | $CH_2CH_3$ |
| 1.215 | $CH_2CH_3$ | 2-methylsulfonylphenyl | H | $CH_2CH_3$ |
| 1.216 | $CH_2CH_3$ | 2-cyanophenyl | H | $CH_2CH_3$ |
| 1.217 | $CH_2CH_3$ | 3-fluorophenyl | H | $CH_2CH_3$ |
| 1.218 | $CH_2CH_3$ | 3-chlorophenyl | H | $CH_2CH_3$ |
| 1.219 | $CH_2CH_3$ | 3-trifluoromethylphenyl | H | $CH_2CH_3$ |
| 1.220 | $CH_2CH_3$ | 3-nitrophenyl | H | $CH_2CH_3$ |
| 1.221 | $CH_2CH_3$ | 3-methylphenyl | H | $CH_2CH_3$ |
| 1.222 | $CH_2CH_3$ | 3-methylsulfonylphenyl | H | $CH_2CH_3$ |
| 1.223 | $CH_2CH_3$ | 3-cyanophenyl | H | $CH_2CH_3$ |
| 1.224 | $CH_2CH_3$ | 4-fluorophenyl | H | $CH_2CH_3$ |
| 1.225 | $CH_2CH_3$ | 4-chlorophenyl | H | $CH_2CH_3$ |
| 1.226 | $CH_2CH_3$ | 4-bromophenyl | H | $CH_2CH_3$ |
| 1.227 | $CH_2CH_3$ | 4-difluoromethoxyphenyl | H | $CH_2CH_3$ |
| 1.228 | $CH_2CH_3$ | 2-fluoro-4-chlorophenyl | H | $CH_2CH_3$ |
| 1.229 | $CH_2CH_3$ | 2-chloro-4-chlorophenyl | H | $CH_2CH_3$ |
| 1.230 | $CH_2CH_3$ | 2-methyl-4-chlorophenyl | H | $CH_2CH_3$ |
| 1.231 | $CH_2CH_3$ | 4-trifluoromethylphenyl | H | $CH_2CH_3$ |
| 1.232 | $CH_2CH_3$ | 4-nitrophenyl | H | $CH_2CH_3$ |
| 1.233 | $CH_2CH_3$ | 4-methylphenyl | H | $CH_2CH_3$ |
| 1.234 | $CH_2CH_3$ | 4-methylsulfonylphenyl | H | $CH_2CH_3$ |
| 1.235 | $CH_2CH_3$ | 4-cyanophenyl | H | $CH_2CH_3$ |
| 1.236 | $OCH_3$ | H | phenyl | H |
| 1.237 | $OCH_3$ | H | 2-fluorophenyl | H |
| 1.238 | $OCH_3$ | H | 2-chlorophenyl | H |
| 1.239 | $OCH_3$ | H | 2-trifluoromethylphenyl | H |
| 1.240 | $OCH_3$ | H | 2-nitrophenyl | H |
| 1.241 | $OCH_3$ | H | 2-methylphenyl | H |
| 1.242 | $OCH_3$ | H | 2-methylsulfonylphenyl | H |
| 1.243 | $OCH_3$ | H | 2-cyanophenyl | H |
| 1.244 | $OCH_3$ | H | 3-fluorophenyl | H |
| 1.245 | $OCH_3$ | H | 3-chlorophenyl | H |
| 1.246 | $OCH_3$ | H | 3-trifluoromethylphenyl | H |
| 1.247 | $OCH_3$ | H | 3-nitrophenyl | H |
| 1.248 | $OCH_3$ | H | 3-methylphenyl | H |
| 1.249 | $OCH_3$ | H | 3-methylsulfonylphenyl | H |
| 1.250 | $OCH_3$ | H | 3-cyanophenyl | H |
| 1.251 | $OCH_3$ | H | 4-fluorophenyl | H |
| 1.252 | $OCH_3$ | H | 4-chlorophenyl | H |
| 1.253 | $OCH_3$ | H | 4-bromophenyl | H |
| 1.254 | $OCH_3$ | H | 4-difluoromethoxyphenyl | H |
| 1.255 | $OCH_3$ | H | 2-fluoro-4-chlorophenyl | H |
| 1.256 | $OCH_3$ | H | 2-chloro-4-chlorophenyl | H |
| 1.257 | $OCH_3$ | H | 2-methyl-4-chlorophenyl | H |
| 1.258 | $OCH_3$ | H | 4-trifluoromethylphenyl | H |
| 1.259 | $OCH_3$ | H | 4-nitrophenyl | H |
| 1.260 | $OCH_3$ | H | 4-methylphenyl | H |
| 1.261 | $OCH_3$ | H | 4-methylsulfonylphenyl | H |
| 1.262 | $OCH_3$ | H | 4-cyanophenyl | H |

Table 2: This table discloses the 262 compounds of the formula I, wherein $R^9$ is $CH_2CH_3$, $R^5$, $R^6$, $R^7$ and $R^8$ are hydrogen, G is hydrogen and $R^1$, $R^2$, $R^3$ and $R^4$ are as defined in Table 1.

Table 3: This table discloses the 262 compounds of the formula I, wherein $R^9$ is $n-C_3H_7$, $R^5$, $R^6$, $R^7$ and $R^8$ are hydrogen, G is hydrogen and $R^1$, $R^2$, $R^3$ and $R^4$ are as defined in Table 1.

Table 4: This table discloses the 262 compounds of the formula I, wherein $R^9$ is $i-C_3H_7$, $R^5$, $R^6$, $R^7$ and $R^8$ are hydrogen, G is hydrogen and $R^1$, $R^2$, $R^3$ and $R^4$ are as defined in Table 1.

Table 5: This table discloses the 262 compounds of the formula I, wherein $R^9$ is allyl, $R^5$, $R^6$, $R^7$ and $R^8$ are hydrogen, G is hydrogen and $R^1$, $R^2$, $R^3$ and $R^4$ are as defined in Table 1.

Table 6: This table discloses the 262 compounds of the formula I, wherein $R^9$ is benzyl, $R^5$, $R^6$, $R^7$ and $R^8$ are hydrogen, G is hydrogen and $R^1$, $R^2$, $R^3$ and $R^4$ are as defined in Table 1.

Table 7: This table discloses the 262 compounds of the formula I, wherein $R^9$ is $C(=O)-CH_3$, $R^5$, $R^6$, $R^7$ and $R^8$ are hydrogen, G is hydrogen and $R^1$, $R^2$, $R^3$ and $R^4$ are as defined in Table 1.

Table 8: This table discloses the 262 compounds of the formula I, wherein $R^9$ is $C(=O)-CH_2CH_3$, $R^5$, $R^6$, $R^7$ and $R^8$ are hydrogen, G is hydrogen and $R^1$, $R^2$, $R^3$ and $R^4$ are as defined in Table 1.

Table 9: This table discloses the 262 compounds of the formula I, wherein $R^9$ is $C(=O)-n-C_3H_7$, $R^5$, $R^6$, $R^7$ and $R^8$ are hydrogen, G is hydrogen and $R^1$, $R^2$, $R^3$ and $R^4$ are as defined in Table 1.

Table 10: This table discloses the 262 compounds of the formula I, wherein $R^9$ is $C(=O)O-CH_3$, $R^5$, $R^6$, $R^7$ and $R^8$ are hydrogen, G is hydrogen and $R^1$, $R^2$, $R^3$ and $R^4$ are as defined in Table 1.

Table 11: This table discloses the 262 compounds of the formula I, wherein $R^9$ is $C(=O)O-CH_2CH_3$, $R^5$, $R^6$, $R^7$ and $R^8$ are hydrogen, G is hydrogen and $R^1$, $R^2$, $R^3$ and $R^4$ are as defined in Table 1.

Table 12: This table discloses the 262 compounds of the formula I, wherein $R^9$ is $C(=O)O-n-C_3H_7$, $R^5$, $R^6$, $R^7$ and $R^8$ are hydrogen, G is hydrogen and $R^1$, $R^2$, $R^3$ and $R^4$ are as defined in Table 1.

Table 13: This table discloses the 262 compounds of the formula I, wherein $R^9$ is $C(=O)NH-CH_3$, $R^5$, $R^6$, $R^7$ and $R^8$ are hydrogen, G is hydrogen and $R^1$, $R^2$, $R^3$ and $R^4$ are as defined in Table 1.

Table 14: This table discloses the 262 compounds of the formula I, wherein $R^9$ is $C(=O)NH-CH_2CH_3$, $R^5$, $R^6$, $R^7$ and $R^8$ are hydrogen, G is hydrogen and $R^1$, $R^2$, $R^3$ and $R^4$ are as defined in Table 1.

Table 15: This table discloses the 262 compounds of the formula I, wherein $R^9$ is $C(=O)NH-n-C_3H_7$, $R^5$, $R^6$, $R^7$ and $R^8$ are hydrogen, G is hydrogen and $R^1$, $R^2$, $R^3$ and $R^4$ are as defined in Table 1.

Table 16: This table discloses the 262 compounds of the formula I, wherein $R^5$, $R^6$, $R^7$, Wand $R^9$ are hydrogen, G is hydrogen and $R^1$, $R^2$, $R^3$ and $R^4$ are as defined in Table 1.

Table 17: This table discloses the 262 compounds of the formula I, wherein $R^9$ is $CH_2-O-CH_3$, $R^5$, $R^6$, $R^7$ and $R^8$ are hydrogen, G is hydrogen and $R^1$, $R^2$, $R^3$ and $R^4$ are as defined in Table 1.

Table 18: This table discloses the 262 compounds of the formula I, wherein $R^9$ is $CH_2-O-C_2H_5$, $R^5$, $R^6$, $R^7$ and $R^8$ are hydrogen, G is hydrogen and $R^1$, $R^2$, $R^3$ and $R^4$ are as defined in Table 1.

Table 19: This table discloses the 262 compounds of the formula I, wherein $R^9$ is $CH_2-O-C_2H_4-O-CH_3$, $R^5$, $R^6$, $R^7$ and $R^8$ are hydrogen, G is hydrogen and $R^1$, $R^2$, $R^3$ and $R^4$ are as defined in Table 1.

Table 20: This table discloses the 262 compounds of the formula I, wherein $R^9$ is hydrogen, $R^5$, $R^6$, $R^7$ and $R^8$ are $CH_3$, G is hydrogen and $R^1$, $R^2$, $R^3$ and $R^4$ are as defined in Table 1.

Table 21: This table discloses the 262 compounds of the formula I, wherein $R^9$ is $CH_3$, $R^5$, $R^6$, $R^7$ and $R^8$ are $CH_3$, G is hydrogen and $R^1$, $R^2$, $R^3$ and $R^4$ are as defined in Table 1.

Table 22: This table discloses the 262 compounds of the formula I, wherein $R^9$ is $C_2H_5$, $R^5$, $R^6$, $R^7$ and $R^8$ are $CH_3$, G is hydrogen and $R^1$, $R^2$, $R^3$ and $R^4$ are as defined in Table 1.

BIOLOGICAL EXAMPLES

Example A

Monocotyledonous and dicotyledonous test plants are sown in standard soil in pots. After cultivation for one day (pre-emergence) or after 10 days cultivation (post-emergence) under controlled conditions in a glasshouse, the plants are sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants are then grown in a greenhouse under optimum conditions until, 15 days later for post-emergence and 20 days for pre-emergence, the test is evaluated (100=total damage to plant; 0=no damage to plant).
Test Plants:
*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)
Pre-Emergence Activity

| Compound Number | Rate g/ha | ALOMY | AVEFA | LOLPE | SETFA | DIGSA | ECHOG |
|---|---|---|---|---|---|---|---|
| T9 | 250 | 0 | 60 | 30 | 0 | 0 | 10 |
| T23 | 250 | 40 | 50 | 40 | 100 | 100 | 100 |
| P16 | 250 | 30 | 30 | 50 | 10 | 0 | 20 |
| P18 | 250 | 60 | 70 | 70 | 20 | 20 | 30 |
| P29 | 250 | 20 | 50 | 10 | 0 | 20 | 60 |
| P43 | 250 | 80 | 70 | 70 | 80 | 90 | 80 |
| P53 | 250 | 0 | 30 | 20 | 40 | 60 | 50 |
| P67 | 250 | 0 | 40 | 10 | 50 | 20 | 60 |
| P70 | 250 | 70 | 70 | 30 | 100 | 100 | 100 |

Post-Emergence Activity

| Compound Number | Rate g/ha | ALOMY | AVEFA | LOLPE | SETFA | DIGSA | ECHOG |
|---|---|---|---|---|---|---|---|
| T9 | 125 | 90 | 80 | 50 | 90 | 100 | 100 |
| T23 | 125 | 100 | 100 | 80 | 100 | 100 | 100 |
| P16 | 125 | 70 | 30 | 20 | 50 | 50 | 50 |
| P18 | 125 | 70 | 60 | 70 | 60 | 80 | 80 |
| P29 | 125 | 90 | 90 | 80 | 90 | 100 | 100 |
| P43 | 125 | 60 | 40 | 70 | 50 | 70 | 60 |
| P53 | 125 | 20 | 0 | 0 | 50 | 60 | 60 |
| P67 | 125 | 40 | 60 | 40 | 70 | 80 | 70 |
| P70 | 125 | 0 | 10 | 0 | 90 | 100 | 100 |

Example B

Seeds of a variety of test species are sown in standard soil in pots. After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants are then grown in a glasshouse under controlled conditions in a glasshouse (at 24/16° C., day/night; 14 hours light; 65% humidity) and watered twice daily. After 13 days for pre and post-emergence, the test is evaluated (100=total damage to plant; 0=no damage to plant).

Test Plants:

*Setaria faberi* (SETFA), *Alopecurus myosuroides* (ALOMY), *Echinochloa crus-galli* (ECHCG), *Avena fatua* (AVEFA)

Post-Emergence Activity

| Compound Number | Rate g/ha | SETFA | ALOMY | ECHCG | AVEFA |
|---|---|---|---|---|---|
| T2 | 1000 | 30 | 60 | 0 | 40 |
| T3 | 1000 | 80 | 40 | 0 | 0 |
| T4 | 1000 | 90 | 90 | 100 | 100 |
| T5 | 1000 | 90 | 100 | 100 | 90 |
| T12 | 1000 | 90 | 70 | 20 | 80 |
| T23 | 250 | 100 | 70 | 90 | 90 |
| P16 | 1000 | 90 | 70 | 40 | 50 |
| P18 | 1000 | 100 | 100 | 100 | 90 |
| P22 | 1000 | 90 | 90 | 100 | 90 |
| P25 | 1000 | 60 | 60 | 80 | 0 |
| P29 | 1000 | 100 | 70 | 100 | 90 |
| P34 | 1000 | 20 | 30 | 20 | 40 |
| P39 | 1000 | 60 | 0 | 30 | 0 |
| P43 | 1000 | 100 | 100 | 100 | 90 |
| P44 | 1000 | 30 | 20 | 30 | 10 |
| P48 | 1000 | 90 | 100 | 80 | 80 |
| P49 | 1000 | 80 | 80 | 70 | 80 |
| P53 | 250 | 80 | 0 | 0 | 0 |
| P55 | 250 | 60 | 10 | 40 | 0 |
| P66 | 250 | 10 | 30 | 0 | 10 |
| P67 | 250 | 100 | 80 | 70 | 60 |
| P69 | 250 | 100 | 40 | 90 | 30 |
| P70 | 250 | 100 | 90 | 100 | 90 |

Post-Emergence Activity

| Compound Number | Rate g/ha | SETFA | ALOMY | ECHCG | AVEFA |
|---|---|---|---|---|---|
| T2 | 1000 | 100 | 100 | 100 | 90 |
| T3 | 1000 | 70 | 60 | 0 | 0 |
| T4 | 1000 | 100 | 100 | 100 | 90 |
| T5 | 1000 | 90 | 90 | 100 | 60 |
| T9 | 1000 | 100 | 80 | 100 | 90 |
| T12 | 1000 | 90 | 80 | 80 | 90 |
| T15 | 250 | 90 | 60 | 90 | 60 |
| T16 | 250 | 80 | 60 | 60 | 30 |
| T21 | 250 | 80 | 80 | 90 | 60 |
| T22 | 250 | 80 | 60 | 80 | 40 |
| T23 | 250 | 100 | 100 | 100 | 100 |
| P16 | 1000 | 100 | 100 | 100 | 80 |
| P18 | 1000 | 100 | 100 | 100 | 90 |
| P22 | 1000 | 70 | 90 | 100 | 60 |
| P25 | 1000 | 0 | 50 | 40 | 0 |
| P29 | 1000 | 100 | 100 | 100 | 100 |
| P32 | 1000 | 90 | 70 | 80 | 60 |
| P34 | 1000 | 60 | 10 | 40 | 0 |
| P39 | 1000 | 50 | 10 | 40 | 0 |
| P43 | 1000 | 90 | 90 | 90 | 90 |
| P44 | 1000 | 50 | 50 | 0 | 0 |
| P48 | 1000 | 80 | 80 | 80 | 10 |
| P49 | 1000 | 80 | 90 | 80 | 80 |
| P53 | 250 | 90 | 70 | 90 | 30 |
| P55 | 250 | 80 | 60 | 70 | 60 |
| P56 | 250 | 60 | 20 | 50 | 40 |
| P66 | 250 | 90 | 90 | 100 | 70 |
| P67 | 250 | 90 | 100 | 100 | 60 |
| P68 | 250 | 90 | 70 | 90 | 60 |
| P69 | 250 | 90 | 90 | 90 | 60 |
| P70 | 250 | 100 | 100 | 100 | 100 |
| P71 | 250 | 60 | 0 | 30 | 20 |

What is claimed is:

1. A herbicidal composition, which, in addition to comprising formulation adjuvants, comprises a herbicidally effective amount of a compound of formula I

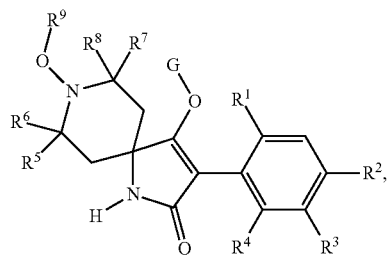

(I)

wherein
G is hydrogen or an agriculturally acceptable metal, sulfonium, ammonium or latentiating group, $R^1$ is hydrogen, methyl, ethyl, n-propyl, iso-propyl, halomethyl, haloethyl, halogen, vinyl, ethynyl, methoxy, ethoxy, halomethoxy or haloethoxy, cyclopropyl or halogenocyclopropyl, $R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, methyl, ethyl, n-propyl, iso-propyl, halomethyl, haloethyl, halogen, vinyl, propenyl, ethynyl, propynyl, methoxy, ethoxy, halomethoxy or haloethoxy, $R^5$, $R^6$, $R^7$ and $R^8$, independently of each other, are hydrogen or methyl, $R^9$ is hydrogen, $C_1$-$C_6$alkyl, $C_1$-$C_6$haloalkyl, $C_1$-$C_6$cyanoalkyl, benzyl, $C_1$-$C_4$alkoxy($C_1$-$C_4$)alkyl, $C_1$-$C_4$alkoxy($C_1$-$C_4$)alkoxy($C_1$-$C_4$)alkyl or a group selected from G, or an agrochemically acceptable salt or N-oxide thereof.

2. A herbicidal composition according to claim 1, wherein in the compounds of formula I $R^1$ is methyl, ethyl, n-propyl, vinyl, ethynyl, halogen, methoxy, ethoxy, halomethoxy, haloethoxy, $R^2$ is methyl, halogen, $C_1$-$C_2$alkoxy, $C_1$-$C_2$haloalkoxy, phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^3$ is hydrogen, $R^4$ is methyl ethyl, n-propyl, vinyl or ethynyl, $R^5$, $R^6$, $R^7$ and $R^8$ are hydrogen, and $R^9$ is hydrogen, $C_1$-$C_6$alkyl, $C_1$-$C_4$alkoxy($C_1$-$C_4$)alkyl, $C_1$-$C_4$alkoxy($C_1$-$C_4$)alkoxy($C_1$-$C_4$)alkyl or a group selected from G.

3. A herbicidal composition according to claim 2, wherein in the compound of the formula I $R^1$ is methyl and $R^2$ is methyl.

4. A herbicidal composition according to claim 1, wherein in the compound of the formula I G is hydrogen, an alkali metal or alkaline earth metal.

5. A herbicidal composition according to claim 1, which, in addition to comprising formulation adjuvants, comprises a herbicidally effective amount of a compound of formula I, optionally a further herbicide and optionally a safener.

6. A method of controlling grasses and weeds in crops of useful plants, which comprises applying a composition comprising a herbicidally effective amount of a compound of formula I to the plants or to the locus thereof.

* * * * *